(12) United States Patent
Benfey et al.

(10) Patent No.: US 7,109,001 B2
(45) Date of Patent: Sep. 19, 2006

(54) COBRA GENE AND USES THEREOF

(75) Inventors: Philip N. Benfey, Chapel Hill, NC (US); Gary Schindelman, Pasadena, CA (US)

(73) Assignee: New York University, New York, NY (US)

( * ) Notice: Subject to any disclaimer, the term of this patent is extended or adjusted under 35 U.S.C. 154(b) by 416 days.

(21) Appl. No.: 10/133,985

(22) Filed: Apr. 25, 2002

(65) Prior Publication Data
US 2005/0223433 A1    Oct. 6, 2005

Related U.S. Application Data

(60) Provisional application No. 60/287,510, filed on Apr. 30, 2001.

(51) Int. Cl.
C12N 15/29 (2006.01)
C12N 15/82 (2006.01)
C12N 5/04 (2006.01)
C12N 15/87 (2006.01)
A01H 5/00 (2006.01)

(52) U.S. Cl. .................. 435/69.1; 435/410; 435/419; 536/23.6; 536/24.1; 800/278; 800/298; 800/287

(58) Field of Classification Search ............... 536/23.1, 536/23.6, 24.1; 800/278, 287, 298; 435/468, 435/69.1, 419, 410
See application file for complete search history.

(56) References Cited

FOREIGN PATENT DOCUMENTS

EP          1033405 A2  *  9/2000

OTHER PUBLICATIONS

Bowie et al, Science 247:1306-1310, 1990.*
McConnell et al, Nature 411 (6838):709-713, 2001.*
Leuchter et al (Sep. 1998, NCBI Accession No. AJ006787).*
Alexandrov et al., N-Geneseq. Database Accession No. AAC48658, SEQ ID No. 58283 of European Patent Application Serial No. EP 1033405-A2 (Sep. 6, 2000).
Roudier et al., "The COBRA Family of Putative GPI-Anchored Proteins in Arabidopsis. A New Fellowship in Expansion," *Plant Physiology* 130:538-548 (2002).
Arioli et al., "Molecular Analysis of Cellulose Biosynthesis in *Arabidopsis*," *Science* 279:717-720 (1998).
Beemster et al., "Analysis of Cell Division and Elongation Underlying the Developmental Acceleration of Root Growth in *Arabidopsis thaliana*," *Plant Physiol.* 116:1515-1526 (1998).
Bender et al., "A Myb Homologue, ATR1, Activates Tryptophan Gene Expression in *Arabidopsis*," *Proc. Natl. Acad. Sci. USA* 95:5655-5660 (1998).
Benfey et al., "Root Development in *Arabidopsis*: Four Mutants with Dramatically Altered Root Morphogenesis," *Development* 119:57-70 (1993).

Bonin et al., "The *MUR1* Gene of *Arabidopsis thaliana* Encodes an Isoform of GDP-D- Mannose-4,6-Dehydratase, Catalyzing the First Step in the *De Novo* Synthesis of GDP-L-Fucose," *Proc. Natl. Acad. Sci. USA* 94:2085-2090 (1997).
Chen et al., "A Rapid Method to Screen for Cell-Wall Mutants Using Discriminant Analysis of Fourier Transform Infrared Spectra," *Plant J.* 16(3):385-392 (1998).
Clough et al., "Floral Dip: A Simplified Method for *Agrobacterium*-Mediated Transformation of *Arabidopsis thaliana*," *Plant J.* 16(6):735-743 (1998).
DiLaurenzio et al., "The *SCARECROW* Gene Regulates an Asymmetric Cell Division That Is Essential for Generating the Radial Organization of the *Arabidopsis* Root," *Cell* 86:423-433 (1996).
Dubois et al., "A Colorimetric Method for Determination of Sugars and Related Substances," *Anal. Chem.* 28:350-356 (1956).
Fagard et al., "*PROCUSTE1* Encodes a Cellulose Synthase Required for Normal Cell Elongation Specifically in Roots and Dark-Grown Hypocotyls of *Arabidopsis*," *Plant Cell* 12:2409-2423 (2000).
Friedrichson et al., "Microdomains of GPI-Anchored Proteins in Living Cells Revealed by Crosslinking," *Nature* 394:802-805 (1998).
Hauser et al., "Conditional Root Expansion Mutants of *Arabidopsis*," *Development* 121:1237-1252 (1995).
Jinn et al., "*HAESA*, An *Arabidopsis* Leucine-Rich Repeat Receptor Kinase, Controls Floral Organ Abscission," *Genes & Dev.* 14:108-117 (2000).
Johnson et al., "An Intrinsic Tonoplast Protein of Protein Storage Vacuoles in Seeds in Structurally Related to a Bacterial Solute Transporter (GlpF)," *Plant Cell* 2:525-532 (1990).
Kim et al., "The *ROTUNDIFOLIA3* Gene of *Arabidopsis thaliana* Encodes a New Member of the Cytochrome P-450 Family That Is Required for the Regulated Polar Elongation of Leaf Cells," *Gene & Dev.* 12:2381-2391 (1998).

(Continued)

*Primary Examiner*—Stuart F. Baum
(74) *Attorney, Agent, or Firm*—Nixon Peabody LLP

(57) ABSTRACT

A method by which many plants control organ shape is by regulated, differential cellular expansion. A gene involved in regulating the expansion of plants cells, such as *Arabidopsis thaliana* root cells is COBRA which encodes a protein with a putative GPI anchor. Plants comprising altered root morphologies may be produced by control of COBRA activity. For example, roots which lack COBRA activity comprise thicker, fatter roots (a CORE or cob phenotype) which are well suited for penetrating dense, compacted soil. Plants lacking COBRA activity may be useful in applications wherein plant growth in areas with dense soil would be beneficial. The present invention comprises the *Arabidopsis thaliana* COBRA gene and COBRA protein and homologues thereof as well as mutated alleles of COBRA. Also provided are anti-COBRA antibodies, transgenic plants which overexpress COBRA and methods for identifying COBRA modulating substances.

13 Claims, 7 Drawing Sheets

OTHER PUBLICATIONS

Konieczny et al., "A Procedure for Mapping *Arabidopsis* Mutations Using Co-Dominant Ecotype-Specific PCR-based Markers," *Plant J.* 4:403-410 (1993).

Leuchter et al., "Isolation of an *Arabidopsis thaliana* cDNA Complementing a *Schizosaccharomyces pombe* Mutant Which is Deficient in Phytochelatin Synthesis (Accession No. AJ006787)," *Plant Physiol.* 117:1526 (1998).

Lukowitz et al., "Cytokinesis in the *Arabidopsis* Embryo Involves the Syntaxin-Related KNOLLE Gene Product," *Cell* 84:61-71 (1996).

Nicol et al., "A Plasma Membrane-Bound Putative Endo-1,4-β-D-Glucanase is Required for Normal Wall Assembly and Cell Elongation in *Arabidopsis*," *EMBO J.* 17:5563-5576 (1998).

Pritchard, "The Control of Cell Expansion in Roots," *New Phytol.* 127:3-26 (1994).

Schindelman et al., "COBRA Encodes a Putative GPI-Anchored Protein, Which Is Polarly Localized and Necessary for Oriented Cell Expansion in *Arabidopsis*," *Genes & Development* 15(9):1115-1127 (2001).

Schultz et al., "GPI-Anchors on Arabinogalactan-Proteins: Implications for Signalling in Plants," *Trend. Plant Sci.* 3:426-431 (1998).

Sherrier et al., Glycosylphosphatidylinositol-Anchored Cell-Surface Proteins from *Arabidopsis, Electrophoresis* 20:2027-2035 (1999).

Taylor et al., "The *Irregular Xylem3* Locus of *Arabidopsis* Encodes a Cellulose Synthase Required for Secondary Cell Wall Synthesis," *Plant Cell* 11:769-779 (1999).

Thompson et al., "Lipid-Linked Proteins of Plants," *Prog. Lipid Res.* 39:19-39 (2000).

Turner et al., "Collapsed Xylem Phenotype of *Arabidopsis* Identifies Mutants Deficient in Cellulose Deposition in the Secondary Cell Wall," *Plant Cell* 9:689-701 (1997).

Udenfriend et al., "How Glycosylphosphatidylinositol-Anchored Membrane Proteins are Made," *Annu. Rev. Biochem.* 64:563-591 (1995).

Udenfriend et al., "Prediction of ω Site in Nascent Precursor of Glycosylphosphatidylinositol Protein," *Methods in Enzymol.* 250:571-582 (1995).

Varma et al., "GPI-Anchored Proteins are Organized in Submicron Domains at the Cell Surface," *Nature* 394:798-801 (1998).

Youl et al., "Arabinogalactan-Proteins from *Nicotiana alata* and *Pyrus communis* Contain Glycosylphosphatidylinositol Membrane Anchors," *Proc. Natl. Acad. Sci. USA* 95:7921-7926 (1998).

Sedbrook et al., "The Arabidopsis *SKU5* Gene Encodes an Extracellular Glycosyl Phosphatidylinositol-Anchored Glycoprotein Involved in Directional Root Growth," *Plant Cell* 14:1635-1648 (2002).

Borner et al., "Prediction of Glycosylphosphatidylinositol-Anchored Proteins in *Arabidopsis*. A Genomic Analysis," *Plant Physiol.* 129:486-499 (2002).

Fu et al., "The ROP2 GTPase Controls the Formation of Cortical Fine F-Actin and the Early Phase of Directional Cell Expansion During *Arabidopsis* Organogenesis," *Plant Cell* 14:777-794 (2002).

\* cited by examiner

```
CACTCCTCCTTCAAGCAAAGCACCTTCCTCTTCTTTTTTGCTCCTCTGAGATTGGTTTAAGATTAAACCAGACCCATCTAAGGGATCTGGAACAAGCTTCG        100

TCTCTGGTTCCACTCTGATCATCAGAGTATTAAAAATGGAGTCTTTCTTCTCCAGATCCACCTCCATCGTCTCCAAATTGAGTTTCTTGGCCTTATGGAT         200
                              M  E  S  F  F  S  R  S  T  S  I  V  S  K  L  S  F  L  A  L  W  I           22
                                                                                             ᴄ(cob-3)
CGTCTTCTTGATTTCTTCATCTTCTTTTACTTCGACAGAAGCATATGATGCGCTTGATCCAGAAGGCAACATTACAATGAAATGGGATGTTATGAGCTGG         300
 V  F  L  I  S  S  S  S  F  T  S  T  E  A  Y  D  A  L  D  P  E  G  N  I  T  M  K  W  D  V  M  S  W         55

ACTCCTGATGGCTATGTTGCCGTGGTTACGATGTTCAACTTCCAGAAATACAGACACATTCAATCTCCAGGATGGACATTAGGTTGGAAATGGGCAAAGA         400
 T  P  D  G  Y  V  A  V  V  T  M  F  N  F  Q  K  Y  R  H  I  Q  S  P  G  W  T  L  G  W  K  W  A  K  K      89

AGGAAGTTATATGGAGTATGGTTGGAGCACAAACAACTGAACAAGGTGATTGTTCAAAGTACAAAGGAAACATACCACATTGTTGTAAGAAGGATCCAAC        500
 E  V  I  W  S  M  V  G  A  Q  T  T  E  Q  G  D  C  S  K  Y  K  G  N  I  P  H  C  C  K  K  D  P  T         122

AGTTGTAGACTTGCTTCCAGGGACTCCTTATAATCAGCAGATTGCTAATTGCTGCAAGGGTGGTGTTATGAACTCATGGGTTCAAGACCCTGCCACTGCG        600
 V  V  D  L  L  P  G  T  P  Y  N  Q  Q  I  A  N  C  C  K  G  G  V  M  N  S  W  V  Q  D  P  A  T  A        155
                                   ₐ(cob-1,cob-2)
GCTAGCTCCTTCCAGATTAGTGTTGGTGCTGCTGGAACCACAAACAAAACCGTTAGGGTCCCAAGAAACTTCACTCTCATGGGACCTGGTCCAGGTTACA        700
 A  S  S  F  Q  I  S  V  G  A  A  G  T  T  N  K  T  V  R  V  P  R  N  F  T  L  M  G  P  G  P  G  Y  T     189

CTTGTGGTCCAGCAAAGATTGTCAGACCAACAAAATTTGTCACGACTGACACACGCAGAACCACTCAAGCTATGATGACATGGAACATTACGTGCACATA        800
 C  G  P  A  K  I  V  R  P  T  K  F  V  T  T  D  T  R  R  T  T  Q  A  M  M  T  W  N  I  T  C  T  Y        222

CTCGCAGTTCCTTGCTCAAAGAACTCCAACTTGCTGTGTTTCTTTATCTTCTTTCTACAATGAAACCATTGTTGGATGTCCAACTTGTGCTTGCGGATGT        900
 S  Q  F  L  A  Q  R  T  P  T  C  C  V  S  L  S  S  F  Y  N  E  T  I  V  G  C  P  T  C  A  C  G  C        255

CAAAACAACAGAACAGAATCCGGTGCCTGCCTCGACCCGGACACACCACACTTAGCCTCGGTTGTGTCACCACCAACAAAGAAAGGAACGGTTTTACCAC        1000
 Q  N  N  R  T  E  S  G  A  C  L  D  P  D  T  P  H  L  A  S  V  V  S  P  P  T  K  K  G  T  V  L  P  P     289

CATTAGTGCAATGCACGAGACACATGTGCCCGATCAGAGTGCATTGGCATGTAAAGCAGAACTACAAAGAGTATTGGCGTGTGAAGATCACAATCACAAA        1100
 L  V  Q  C  T  R  H  M  C  P  I  R  V  H  W  H  V  K  Q  N  Y  K  E  Y  W  R  V  K  I  T  I  T  N        322

CTTCAACTATCGCTTGAACTACACACAATGGAACCTTGTTGCTCAACATCCAAATCTCGACAACATCACTCAAATCTTCAGCTTCAACTACAAATCTCTT        1200
 F  N  Y  R  L  N  Y  T  Q  W  N  L  V  A  Q  H  P  N  L  D  N  I  T  Q  I  F  S  F  N  Y  K  S  L        355

ACTCCTTACGCTGGACTAAACGATACGGCGATGTTATGGGGAGTGAAGTTCTACAACGATTTCTTATCGAAGCAGGTCCTCTTGGGAATGTTCAATCAG        1300
 T  P  Y  A  G  L  N  D  T  A  M  L  W  G  V  K  F  Y  N  D  F  L  S  E  A  G  P  L  G  N  V  Q  S  E     389

AGATTTTGTTCCGTAAAGACCAATCAACCTTCACATTCGAGAAAGGTTGGGCTTTTCCACGAAGGATTTACTTTAATGGAGACAATTGCGTCATGCCTCC        1400
 I  L  F  R  K  D  Q  S  T  F  T  F  E  K  G  W  A  F  P  R  R  I  Y  F  N  G  D  N  C  V  M  P  P        422

TCCAGACTCTTACCCTTTTCTTCCCAACGGTGGTTCCCGGTCACAATTCTCATTCGTCGCCGCCGTGCTCCTCCCTCTTCTTGTCTTTTTCTTCTTCTCT        1500
 P  D  S  Y  P  F  L  P  N  G  G  S  R  S  Q  F  S  F  V  A  A  V  L  L  P  L  L  V  F  F  F  F  S        455

GCCTAATCTCGGATTTACGGTTTTGCCACTGGTTTGCTTAGGGTTACGGCGGAGTGGTATAAACGTTTATTTATGATTCTTTTGTGTCCCACAAAAATTA        1600
 A  STOP                                                                                                  456

TAATCTTTTGATACTTTTTAAAAATATAAATAGTTTTCAA                                                                  1640
```

*FIG. 3C*

SEQUENCE LISTING

<160> NUMBER OF SEQ ID NOS: 6

<210> SEQ ID NO 1
<211> LENGTH: 1371
<212> TYPE: DNA
<213> ORGANISM: Arabidopsis thaliana

<400> SEQUENCE: 1

| | | | | | | |
|---|---|---|---|---|---|---|
| atggagtctt | tcttctccag | atccacctcc | atcgtctcca | aattgagttt | cttggcctta | 60 |
| tggatcgtct | tcttgatttc | ttcatcttct | tttacttcga | cagaagcata | tgatgcgctt | 120 |
| gatccagaag | gcaacattac | aatgaaatgg | gatgttatga | gctggactcc | tgatggctat | 180 |
| gttgccgtgg | ttacgatgtt | caacttccag | aaatacagac | acattcaatc | tccaggatgg | 240 |
| acattaggtt | ggaaatgggc | aaagaaggaa | gttatatgga | gtatggttgg | agcacaaaca | 300 |
| actgaacaag | gtgattgttc | aaagtacaaa | ggaaacatac | cacattgttg | taagaaggat | 360 |
| ccaacagttg | tagacttgct | tccagggact | ccttataatc | agcagattgc | taattgctgc | 420 |
| aagggtggtg | ttatgaactc | atgggttcaa | gaccctgcca | ctgcggctag | ctccttccag | 480 |
| attagtgttg | gtgctgctgg | aaccacaaac | aaaaccgtta | gggtcccaag | aaacttcact | 540 |
| ctcatgggac | ctggtccagg | ttacacttgt | ggtccagcaa | agattgtcag | accaacaaaa | 600 |
| tttgtcacga | ctgacacacg | cagaaccact | caagctatga | tgacatggaa | cattacgtgc | 660 |
| acatactcgc | agttccttgc | tcaaagaact | ccaacttgct | gtgtttcttt | atcttctttc | 720 |
| tacaatgaaa | ccattgttgg | atgtccaact | tgtgcttgcg | gatgtcaaaa | caacagaaca | 780 |
| gaatccggtg | cctgcctcga | cccggacaca | ccacacttag | cctcggttgt | gtcaccacca | 840 |
| acaaagaaag | gaacggtttt | accaccatta | gtgcaatgca | cgagacacat | gtgcccgatc | 900 |
| agagtgcatt | ggcatgtaaa | gcagaactac | aaagagtatt | ggcgtgtgaa | gatcacaatc | 960 |
| acaaacttca | actatcgctt | gaactacaca | caatggaacc | ttgttgctca | acatccaaat | 1020 |
| ctcgacaaca | tcactcaaat | cttcagcttc | aactacaaat | ctcttactcc | ttacgctgga | 1080 |
| ctaaacgata | cggcgatgtt | atggggagtg | aagttctaca | acgatttctt | atcagaagca | 1140 |
| ggtcctcttg | gaatgttca | atcagagatt | ttgttccgta | aagaccaatc | aaccttcaca | 1200 |
| ttcgagaaag | gttgggcttt | tccacgaagg | atttacttta | atggagacaa | ttgcgtcatg | 1260 |
| cctcctccag | actcttaccc | ttttcttccc | aacggtggtt | cccggtcaca | attctcattc | 1320 |
| gtcgccgccg | tgctcctccc | tcttcttgtc | ttttcttct | tctctgccta | a | 1371 |

<210> SEQ ID NO 2
<211> LENGTH: 1371
<212> TYPE: DNA
<213> ORGANISM: Arabidopsis thaliana

<400> SEQUENCE: 2

| | | | | | | |
|---|---|---|---|---|---|---|
| atggagtctt | tcttctccag | atccacctcc | atcgtctcca | aattgagttt | cttggcctta | 60 |
| tggatcgtct | tcttgatttc | ttcatcttct | tttacttcga | cagaagcata | tgatgcgctt | 120 |
| gatccagaag | gcaacattac | aatgaaatgg | gatgttatga | gctggactcc | tgatggctat | 180 |
| gttgccgtgg | ttacgatgtt | caacttccag | aaatacagac | acattcaatc | tccaggatgg | 240 |
| acattaggtt | ggaaatgggc | aaagaaggaa | gttatatgga | gtatggttgg | agcacaaaca | 300 |
| actgaacaag | gtgattgttc | aaagtacaaa | ggaaacatac | cacattgttg | taagaaggat | 360 |
| ccaacagttg | tagacttgct | tccagggact | ccttataatc | agcagattgc | taattgctgc | 420 |

-continued

```
aagggtggtg ttatgaactc atgggttcaa gaccctgcca ctgcggctag ctccttccag      480
attagtgttg gtgctgctag aaccacaaac aaaaccgtta gggtcccaag aaacttcact      540
ctcatgggac ctggtccagg ttacacttgt ggtccagcaa agattgtcag accaacaaaa      600
tttgtcacga ctgacacacg cagaaccact caagctatga tgacatggaa cattacgtgc      660
acatactcgc agttccttgc tcaaagaact ccaacttgct gtgtttcttt atcttctttc      720
tacaatgaaa ccattgttgg atgtccaact tgtgcttgcg gatgtcaaaa caacagaaca      780
gaatccggtg cctgcctcga cccggacaca ccacacttag cctcggttgt gtcaccacca      840
acaaagaaag gaacggtttt accaccatta gtgcaatgca cgagacacat gtgcccgatc      900
agagtgcatt ggcatgtaaa gcagaactac aaagagtatt ggcgtgtgaa gatcacaatc      960
acaaacttca actatcgctt gaactacaca caatggaacc ttgttgctca acatccaaat     1020
ctcgacaaca tcactcaaat cttcagcttc aactacaaat ctcttactcc ttacgctgga     1080
ctaaacgata cggcgatgtt atggggagtg aagttctaca acgatttctt atcagaagca     1140
ggtcctcttg gaatgttcaa tcagagatt tgttccgta aagaccaatc aaccttcaca      1200
ttcgagaaag gttgggcttt ccacgaagg atttacttta atggagacaa ttgcgtcatg      1260
cctcctccag actcttaccc ttttcttccc aacggtggtt cccggtcaca attctcattc      1320
gtcgccgccg tgctcctccc tcttcttgtc tttttcttct tctctgccta a              1371
```

<210> SEQ ID NO 3
<211> LENGTH: 1371
<212> TYPE: DNA
<213> ORGANISM: Arabidopsis thaliana

<400> SEQUENCE: 3

```
atggagtctt tcttctccag atccacctcc atcgtctcca aattgagttt cttggcctta       60
tggatcgtct tcttgatttc ttcatcttct tttacttcga cagaagcata tgatgcgctt      120
gatccagaag gcaacattac aatgaaatgg atgttatga gccggactcc tgatggctat      180
gttgccgtgg ttacgatgtt caacttccag aaatacagac acattcaatc tccaggatgg      240
acattaggtt ggaaatgggc aaagaaggaa gttatatgga gtatggttgg agcacaaaca      300
actgaacaag gtgattgttc aaagtacaaa ggaaacatac cacattgttg taagaaggat      360
ccaacagttg tagacttgct tccagggact ccttataatc agcagattgc taattgctgc      420
aagggtggtg ttatgaactc atgggttcaa gaccctgcca ctgcggctag ctccttccag      480
attagtgttg gtgctgctgg aaccacaaac aaaaccgtta gggtcccaag aaacttcact      540
ctcatgggac ctggtccagg ttacacttgt ggtccagcaa agattgtcag accaacaaaa      600
tttgtcacga ctgacacacg cagaaccact caagctatga tgacatggaa cattacgtgc      660
acatactcgc agttccttgc tcaaagaact ccaacttgct gtgtttcttt atcttctttc      720
tacaatgaaa ccattgttgg atgtccaact tgtgcttgcg gatgtcaaaa caacagaaca      780
gaatccggtg cctgcctcga cccggacaca ccacacttag cctcggttgt gtcaccacca      840
acaaagaaag gaacggtttt accaccatta gtgcaatgca cgagacacat gtgcccgatc      900
agagtgcatt ggcatgtaaa gcagaactac aaagagtatt ggcgtgtgaa gatcacaatc      960
acaaacttca actatcgctt gaactacaca caatggaacc ttgttgctca acatccaaat     1020
ctcgacaaca tcactcaaat cttcagcttc aactacaaat ctcttactcc ttacgctgga     1080
ctaaacgata cggcgatgtt atggggagtg aagttctaca acgatttctt atcagaagca     1140
```

-continued

```
ggtcctcttg ggaatgttca atcagagatt ttgttccgta aagaccaatc aaccttcaca      1200
ttcgagaaag gttgggcttt ccacgaagg atttacttta atggagacaa ttgcgtcatg       1260
cctcctccag actcttaccc ttttcttccc aacggtggtt cccggtcaca attctcattc     1320
gtcgccgccg tgctcctccc tcttcttgtc tttttcttct tctctgccta a              1371
```

<210> SEQ ID NO 4
<211> LENGTH: 456
<212> TYPE: PRT
<213> ORGANISM: Arabidopsis thaliana

<400> SEQUENCE: 4

```
Met Glu Ser Phe Phe Ser Arg Ser Thr Ser Ile Val Ser Lys Leu Ser
  1               5                  10                  15

Phe Leu Ala Leu Trp Ile Val Phe Leu Ile Ser Ser Ser Phe Thr
             20                  25                  30

Ser Thr Glu Ala Tyr Asp Ala Leu Asp Pro Glu Gly Asn Ile Thr Met
         35                  40                  45

Lys Trp Asp Val Met Ser Trp Thr Pro Asp Gly Tyr Val Ala Val Val
     50                  55                  60

Thr Met Phe Asn Phe Gln Lys Tyr Arg His Ile Gln Ser Pro Gly Trp
 65                  70                  75                  80

Thr Leu Gly Trp Lys Trp Ala Lys Lys Glu Val Ile Trp Ser Met Val
                 85                  90                  95

Gly Ala Gln Thr Thr Glu Gln Gly Asp Cys Ser Lys Tyr Lys Gly Asn
            100                 105                 110

Ile Pro His Cys Cys Lys Lys Asp Pro Thr Val Val Asp Leu Leu Pro
        115                 120                 125

Gly Thr Pro Tyr Asn Gln Gln Ile Ala Asn Cys Cys Lys Gly Gly Val
    130                 135                 140

Met Asn Ser Trp Val Gln Asp Pro Ala Thr Ala Ala Ser Ser Phe Gln
145                 150                 155                 160

Ile Ser Val Gly Ala Ala Gly Thr Thr Asn Lys Thr Val Arg Val Pro
                165                 170                 175

Arg Asn Phe Thr Leu Met Gly Pro Gly Pro Gly Tyr Thr Cys Gly Pro
            180                 185                 190

Ala Lys Ile Val Arg Pro Thr Lys Phe Val Thr Thr Asp Thr Arg Arg
        195                 200                 205

Thr Thr Gln Ala Met Met Thr Trp Asn Ile Thr Cys Thr Tyr Ser Gln
    210                 215                 220

Phe Leu Ala Gln Arg Thr Pro Thr Cys Cys Val Ser Leu Ser Ser Phe
225                 230                 235                 240

Tyr Asn Glu Thr Ile Val Gly Cys Pro Thr Cys Ala Cys Gly Cys Gln
                245                 250                 255

Asn Asn Arg Thr Glu Ser Gly Ala Cys Leu Asp Pro Asp Thr Pro His
            260                 265                 270

Leu Ala Ser Val Val Ser Pro Pro Thr Lys Lys Gly Thr Val Leu Pro
        275                 280                 285

Pro Leu Val Gln Cys Thr Arg His Met Cys Pro Ile Arg Val His Trp
    290                 295                 300

His Val Lys Gln Asn Tyr Lys Glu Tyr Trp Arg Val Lys Ile Thr Ile
305                 310                 315                 320

Thr Asn Phe Asn Tyr Arg Leu Asn Tyr Thr Gln Trp Asn Leu Val Ala
                325                 330                 335
```

```
Gln His Pro Asn Leu Asp Asn Ile Thr Gln Ile Phe Ser Phe Asn Tyr
            340                 345                 350

Lys Ser Leu Thr Pro Tyr Ala Gly Leu Asn Asp Thr Ala Met Leu Trp
            355                 360                 365

Gly Val Lys Phe Tyr Asn Asp Phe Leu Ser Glu Ala Gly Pro Leu Gly
            370                 375                 380

Asn Val Gln Ser Glu Ile Leu Phe Arg Lys Asp Gln Ser Thr Phe Thr
385                 390                 395                 400

Phe Glu Lys Gly Trp Ala Phe Pro Arg Arg Ile Tyr Phe Asn Gly Asp
            405                 410                 415

Asn Cys Val Met Pro Pro Asp Ser Tyr Pro Phe Leu Pro Asn Gly
            420                 425                 430

Gly Ser Arg Ser Gln Phe Ser Phe Val Ala Ala Val Leu Leu Pro Leu
            435                 440                 445

Leu Val Phe Phe Phe Ser Ala
    450                 455

<210> SEQ ID NO 5
<211> LENGTH: 456
<212> TYPE: PRT
<213> ORGANISM: Arabidopsis thaliana

<400> SEQUENCE: 5

Met Glu Ser Phe Phe Ser Arg Ser Thr Ser Ile Val Ser Lys Leu Ser
 1               5                  10                  15

Phe Leu Ala Leu Trp Ile Val Phe Leu Ile Ser Ser Ser Ser Phe Thr
            20                  25                  30

Ser Thr Glu Ala Tyr Asp Ala Leu Asp Pro Glu Gly Asn Ile Thr Met
            35                  40                  45

Lys Trp Asp Val Met Ser Trp Thr Pro Asp Gly Tyr Val Ala Val Val
    50                  55                  60

Thr Met Phe Asn Phe Gln Lys Tyr Arg His Ile Gln Ser Pro Gly Trp
 65                  70                  75                  80

Thr Leu Gly Trp Lys Trp Ala Lys Lys Glu Val Ile Trp Ser Met Val
            85                  90                  95

Gly Ala Gln Thr Thr Glu Gln Gly Asp Cys Ser Lys Tyr Lys Gly Asn
            100                 105                 110

Ile Pro His Cys Cys Lys Lys Asp Pro Thr Val Val Asp Leu Leu Pro
            115                 120                 125

Gly Thr Pro Tyr Asn Gln Gln Ile Ala Asn Cys Cys Lys Gly Gly Val
            130                 135                 140

Met Asn Ser Trp Val Gln Asp Pro Ala Thr Ala Ala Ser Ser Phe Gln
145                 150                 155                 160

Ile Ser Val Gly Ala Ala Arg Thr Thr Asn Lys Thr Val Arg Val Pro
            165                 170                 175

Arg Asn Phe Thr Leu Met Gly Pro Gly Pro Gly Tyr Thr Cys Gly Pro
            180                 185                 190

Ala Lys Ile Val Arg Pro Thr Lys Phe Val Thr Thr Asp Thr Arg Arg
            195                 200                 205

Thr Thr Gln Ala Met Met Thr Trp Asn Ile Thr Cys Thr Tyr Ser Gln
            210                 215                 220

Phe Leu Ala Gln Arg Thr Pro Thr Cys Cys Val Ser Leu Ser Ser Phe
225                 230                 235                 240

Tyr Asn Glu Thr Ile Val Gly Cys Pro Thr Cys Ala Cys Gly Cys Gln
            245                 250                 255
```

-continued

Asn Asn Arg Thr Glu Ser Gly Ala Cys Leu Asp Pro Asp Thr Pro His
            260                 265                 270

Leu Ala Ser Val Val Ser Pro Thr Lys Lys Gly Thr Val Leu Pro
        275                 280                 285

Pro Leu Val Gln Cys Thr Arg His Met Cys Pro Ile Arg Val His Trp
    290                 295                 300

His Val Lys Gln Asn Tyr Lys Glu Tyr Trp Arg Val Lys Ile Thr Ile
305                 310                 315                 320

Thr Asn Phe Asn Tyr Arg Leu Asn Tyr Thr Gln Trp Asn Leu Val Ala
                325                 330                 335

Gln His Pro Asn Leu Asp Asn Ile Thr Gln Ile Phe Ser Phe Asn Tyr
            340                 345                 350

Lys Ser Leu Thr Pro Tyr Ala Gly Leu Asn Asp Thr Ala Met Leu Trp
        355                 360                 365

Gly Val Lys Phe Tyr Asn Asp Phe Leu Ser Glu Ala Gly Pro Leu Gly
    370                 375                 380

Asn Val Gln Ser Glu Ile Leu Phe Arg Lys Asp Gln Ser Thr Phe Thr
385                 390                 395                 400

Phe Glu Lys Gly Trp Ala Phe Pro Arg Arg Ile Tyr Phe Asn Gly Asp
                405                 410                 415

Asn Cys Val Met Pro Pro Asp Ser Tyr Pro Phe Leu Pro Asn Gly
            420                 425                 430

Gly Ser Arg Ser Gln Phe Ser Phe Val Ala Ala Val Leu Leu Pro Leu
        435                 440                 445

Leu Val Phe Phe Phe Ser Ala
    450                 455

<210> SEQ ID NO 6
<211> LENGTH: 456
<212> TYPE: PRT
<213> ORGANISM: Arabidopsis thaliana

<400> SEQUENCE: 6

Met Glu Ser Phe Phe Ser Arg Ser Thr Ser Ile Val Ser Lys Leu Ser
1               5                   10                  15

Phe Leu Ala Leu Trp Ile Val Phe Leu Ile Ser Ser Ser Ser Phe Thr
            20                  25                  30

Ser Thr Glu Ala Tyr Asp Ala Leu Asp Pro Glu Gly Asn Ile Thr Met
        35                  40                  45

Lys Trp Asp Val Met Ser Arg Thr Pro Asp Gly Tyr Val Ala Val Val
    50                  55                  60

Thr Met Phe Asn Phe Gln Lys Tyr Arg His Ile Gln Ser Pro Gly Trp
65                  70                  75                  80

Thr Leu Gly Trp Lys Trp Ala Lys Lys Glu Val Ile Trp Ser Met Val
                85                  90                  95

Gly Ala Gln Thr Thr Glu Gln Gly Asp Cys Ser Lys Tyr Lys Gly Asn
            100                 105                 110

Ile Pro His Cys Cys Lys Lys Asp Pro Thr Val Val Asp Leu Leu Pro
        115                 120                 125

Gly Thr Pro Tyr Asn Gln Gln Ile Ala Asn Cys Cys Lys Gly Gly Val
    130                 135                 140

Met Asn Ser Trp Val Gln Asp Pro Ala Thr Ala Ala Ser Ser Phe Gln
145                 150                 155                 160

Ile Ser Val Gly Ala Ala Gly Thr Thr Asn Lys Thr Val Arg Val Pro

-continued

```
                165               170               175
Arg Asn Phe Thr Leu Met Gly Pro Gly Pro Gly Tyr Thr Cys Gly Pro
            180               185               190
Ala Lys Ile Val Arg Pro Thr Lys Phe Val Thr Thr Asp Thr Arg Arg
            195               200               205
Thr Thr Gln Ala Met Met Thr Trp Asn Ile Thr Cys Thr Tyr Ser Gln
            210               215               220
Phe Leu Ala Gln Arg Thr Pro Thr Cys Cys Val Ser Leu Ser Ser Phe
225             230               235               240
Tyr Asn Glu Thr Ile Val Gly Cys Pro Thr Cys Ala Cys Gly Cys Gln
            245               250               255
Asn Asn Arg Thr Glu Ser Gly Ala Cys Leu Asp Pro Asp Thr Pro His
            260               265               270
Leu Ala Ser Val Val Ser Pro Pro Thr Lys Lys Gly Thr Val Leu Pro
            275               280               285
Pro Leu Val Gln Cys Thr Arg His Met Cys Pro Ile Arg Val His Trp
    290               295               300
His Val Lys Gln Asn Tyr Lys Glu Tyr Trp Arg Val Lys Ile Thr Ile
305             310               315               320
Thr Asn Phe Asn Tyr Arg Leu Asn Tyr Thr Gln Trp Asn Leu Val Ala
            325               330               335
Gln His Pro Asn Leu Asp Asn Ile Thr Gln Ile Phe Ser Phe Asn Tyr
            340               345               350
Lys Ser Leu Thr Pro Tyr Ala Gly Leu Asn Asp Thr Ala Met Leu Trp
            355               360               365
Gly Val Lys Phe Tyr Asn Asp Phe Leu Ser Glu Ala Gly Pro Leu Gly
    370               375               380
Asn Val Gln Ser Glu Ile Leu Phe Arg Lys Asp Gln Ser Thr Phe Thr
385             390               395               400
Phe Glu Lys Gly Trp Ala Phe Pro Arg Arg Ile Tyr Phe Asn Gly Asp
            405               410               415
Asn Cys Val Met Pro Pro Pro Asp Ser Tyr Pro Phe Leu Pro Asn Gly
            420               425               430
Gly Ser Arg Ser Gln Phe Ser Phe Val Ala Ala Val Leu Leu Pro Leu
            435               440               445
Leu Val Phe Phe Phe Ser Ala
    450               455
```

COBRA GENE AND USES THEREOF

This application claims priority from U.S. Provisional Application Ser. No. 60/287,510, filed Apr. 30, 2001, which is hereby incorporated by reference in its entirety.

The present invention was developed with governmental funding under National Science Foundation Grant No. 9604489. The U.S. Government may have certain rights in this invention.

FIELD OF THE INVENTION

The present invention comprises the COBRA gene, mutant alleles of COBRA, COBRA protein and uses thereof. Also provided are methods of synthesizing COBRA, antibodies which recognize the protein and transgenic plants which overexpress COBRA or lack a fully functional COBRA gene.

SUMMARY OF THE INVENTION

The present invention comprises an isolated nucleic acid comprising 20 or more contiguous nucleotides wherein said nucleic acid comprises at least 70% identity to a reference nucleotide sequence which is a member selected from the group consisting of SEQ ID NOs. 1–3, as well as an isolated nucleic acid of 20 or more contiguous nucleotides which encodes a protein comprising an amino acid sequence with at least 70% homology or identity to a reference amino acid sequence selected from the group consisting of SEQ ID NOs. 4–6 wherein identity or homology is determined using a BLASTN algorithm or BLASTP algorithm, respectively, where parameters of the algorithm are selected to give the largest match between the sequences tested, over the entire length of the selected reference sequence. The invention also includes an isolated host cell transformed or transfected with the nucleic acids.

The invention also comprises an isolated polypeptide of 20 or more contiguous amino acids comprising at least 70% homology or identity to a reference amino acid sequence selected from the group consisting of SEQ ID NOs. 4–6 wherein homology or identity is determined by using a BLASTP algorithm where parameters of the algorithm are selected to give the largest match between the sequences tested over the entire length of the selected reference sequence.

The invention also includes an isolated host cell comprising the polypeptides as well as methods of producing the polypeptides. Additionally, the invention comprises anti-COBRA antibodies and transgenic plants which overexpress or underexpress COBRA or comprise a mutated COBRA gene.

Methods of overexpressing heterologous proteins in a plant root (e.g, a plant root growing tip) are also provided along with methods of identifying substances that modulate COBRA activity.

BACKGROUND OF THE INVENTION

To control organ shape, plant cells expand differentially. The organization of the cellulose microfibrils in the cell wall is a key determinant of differential expansion. Mutations in the COBRA (COB) gene of *Arabidopsis thaliana*, known to affect the orientation of cell expansion in the root, are reported here to reduce the amount of crystalline cellulose in cell walls in the root growth zone. The COB gene, identified by map-based cloning, contains a sequence motif found in proteins that are anchored to the extracellular surface of the plasma membrane through a glycosylphosphatidylinositol (GPI) linkage. In animal cells, this lipid linkage is known to confer polar localization to proteins. The COB protein was detected predominately on the longitudinal sides of root cells in the zone of rapid elongation. Moreover, COB RNA levels are dramatically upregulated in cells entering the zone of rapid elongation. Based on these results, models are proposed for the role of COB as a regulator of oriented cell expansion.

Because there is no morphogenetic movement of plant cells, control of the three-dimensional structure of organs is only through regulation of cell division and cell expansion. Distinct from most other eukaryotes, after division, plant cells dramatically increase their size achieving volumes that can be hundreds of times their original size (Cosgrove, D. J., Annu. Rev. Cell. Dev. Biol. 13: 171–201, 1997). For plant organs to attain their final morphology and function properly, constituent cells must tightly regulate the way in which they expand. The orientation and extent of an individual cell's expansion are key parameters in determining its size and shape, yet little is known about the molecular mechanisms that regulate either aspect of cell expansion.

Although cell expansion is driven by cell turgor, all evidence indicates that neither water flow nor solute influx to maintain turgor is the primary determinant of the extent or direction of cell expansion (Pritchard, J., New Phytol. 127: 3–26, 1994); rather, the plant cell wall is believed to be the regulator of both. The plant cell wall comprises an array of para-crystalline cellulose microfibrils, which are associated with cross-linking glycans (e.g., hemicellulose) and embedded in a matrix of pectin and small amounts of protein (McCann, M. C., et al., "Architecture of the primary cell wall." in *The cytoskeletal basis of plant growth and form* (ed, C. W. Lloyd), pp. 109–129. Academic Press, London, 1991; Carpita, N. C., et al., Plant J. 3, 1–30, 1993). The polysaccharides of the growing plant cell wall are mostly long-chained polymers that form a cohesive network through non-covalent lateral associations and physical entanglements (Cosgrove, D. J., Ann. Rev. Plant Physiol. Plant Mol. Biol. 50: 391–417, 1999). The cell wall's ability to withstand enormous osmotic pressure while readjusting the arrangement of these constituent polymers appears to be critical to the expansion process.

Regulation of the direction in which a cell expands involves oriented control of cell wall extension as well as polarized deposition of new wall materials (Carpita, N. C., et al., Plant J. 3, 1–30, 1993). Biophysical considerations indicate that there must be a component in the expanding walls that resists the osmotic pressure, thereby channeling the direction of cell elongation. Most evidence points to cellulose microfibrils as the primary load-bearing component of the expanding cell wall performing this function (Pritchard, J., New Phytol. 127: 3–26, 1994). In many cell types, cellulose microfibrils have been shown to be oriented perpendicular to the primary direction of expansion, analogous to hoops around a barrel (Green, P. B., Ann. Rev. Plant. Physiol. 51–82, 1980; Giddings, T. H. J., et al., "Microtubule-mediated control of microfibril deposition: A re-examination of the hypothesis" in *The cytoskeletal basis of plant growth and form* (ed, C. W. Lloyd), pp. 85–99. Academic, London, 1991). Therefore, to regulate the orientation of cell expansion, the cell must be able to control the deposition and spatial organization of cellulose microfibrils as well as rearrange bonds to allow the wall to yield to or resist the osmotic pressure. Unlike pectins and cross-linking glycans, which are made in the cytoplasm and transported out to the wall via the Golgi apparatus (Gibeaut, D. M., et al., FASEB J. 8: 904–915, 1994), cellulose microfibrils are synthesized at the cell membrane-cell wall interface (Delmer, D. P., Plant Mol. Biol. 50: 245–276, 1999). The cellulose microfibrils that are spooled around plant cells are generated by multimeric protein complexes in the plasma membrane commonly referred to as the "terminal complexes" or "particle rosettes". About three dozen individual polymer chains of (1–4)-β-D-glucans are synthesized and subsequently crystallized into a microfibril (Delmer, D. P., Plant Mol. Biol. 50: 245–276, 1999). The process of microfibril crystallization may be facilitated by a subunit of the rosette complex (Delmer, D. P., et al., Plant Cell 7: 987–1000, 1995). Recently, genes have been identified that are involved either in the synthesis of cellulose (Arioli, T., et al., Science 279: 717–720, 1998; Pear, J. R., et al., Proc. Natl. Acad. Sci. USA. 93: 12637–12642, 1996; Turner, S. R., et al., Plant Cell 9: 689–701, 1997; Taylor, N. G., et al., Plant Cell 11: 769–780, 1999; Fagard, M., et al., The Plant Cell, 12, 2000 (in press)) or of non-cellulosic polysaccharide components at the Golgi apparatus or involved in their secretion to the wall (Lukowitz, et al., Cell 84, 61–71, 1996; Bonin, C. P., et al., Proc. Natl. Acad. Sci. USA 94: 2085–2090, 1997; Nicol, F., et al., EMBO J. 17: 5563–5576, 1998; Edwards, M. E., et al., Plant J. 19, 691–697, 1999; Perrin, R. M., et al., Science 284: 1976–1979, 1999; Gibeaut, D. M., Plant Physiol. Biochem. 38: 69–80, 2000). Genes and their products have also been identified that function in rearranging bonds in the cell wall to allow for extensibility (Cosgrove, D. J., Ann. Rev. Plant Physiol. Plant Mol. Biol. 50: 391–417, 1999). In particular, expansins are a family of proteins involved in the disruption of the non-covalent bonds between cellulose microfibrils and cross-linking glycans, causing rapid induction of wall extension (McQueen-Mason, S., et al., Proc. Natl. Acad. Sci. USA 91: 6574–6578, 1994). However, regulation of the orientation or extent of expansion is still poorly understood at the molecular level. To further understand the molecular mechanisms involved in cell expansion we have cloned the COBRA (COB) gene and determined its pattern of expression in roots. Initially cobra, a member of the conditional root expansion (CORE) class of mutants, was isolated in a screen for *Arabidopsis* seedlings with abnormally expanded roots (Benfey, P. N., et al., Development 119: 57–70, 1993). The phenotype of all CORE mutants is conditional on the root growing in the presence of high concentrations of sucrose or other conditions that stimulate rapid root growth (Hauser, M. T., et al., Development 121: 1237–1252, 1995). Root cells in cob appear to be expanded more in the radial than the longitudinal orientation while maintaining cell volume, indicating a role for COBRA in regulating the orientation of cell expansion. Here we report that COB encodes a putative GPI-anchored protein that is localized primarily in the plasma membrane of the longitudinal sides of root cells, and plays a role in determining the orientation of cell expansion.

Figure 1A:
FIG. 1(A-F). Phenotypic analysis of cobra. Wild-type (A) and cob-1 (B) seedlings oriented vertically, grown for 10 days on nutrient agar medium containing 4.5% sucrose. The conditional nature of cob can be seen in the lateral root, which has grown into the agar, thereby slowing its growth (arrowhead). Cleared whole mount of wild-type root viewed with Nomarski optics (C). Arrowhead indicates the region where rapid longitudinal expansion begins. Longitudinal section of cob root stained with toluidine blue (D). Abnormal lateral expansion is most apparent in the epidermis (arrowhead). (E and F) Polarized-light micrographs. In wild type, strong retardance is observed in cell walls throughout the root, both in cross-sectioned walls (arrow) and in longitudinal faces of cells in the plane of section (E; arrowhead). In cob-1 there is little retardance detected in the growing region of the root, in either the crosswalls or the longitudinal faces (bracket) indicating a reduction in crystalline cellulose microfibrils in this region (F). Bars A and B=0.25 cm, C–F=50 μm FIG. 2(A-B). FTIR analysis of cell walls prepared from wild-type and cob-1 roots, grown in the presence or absence of sucrose. Exploratory PCA (see Materials and Methods of Example 1) was performed using 30 FTIR spectra from each population.

(A) PC1 clearly discriminates wild-type spectra from cob-1 spectra, when the plants have been grown in the presence of 3% sucrose. Axes represent the mean values for the population. The corresponding loading (below) has features characteristic of cellulose and protein (peaks of interest are marked). Cellulose peaks are negatively correlated, indicating that cob-1 is cellulose-deficient relative to wild type.

(B) PC1 discriminates between spectra obtained from cob-1 roots grown in the presence or absence of sucrose. The corresponding loading also has features of cellulose and protein (peaks of interest are marked). Cellulose peaks are positively correlated indicating that cob-1 grown in the presence of sucrose is cellulose-deficient relative to cob-1 grown in the absence of sucrose.

FIG. 3(A-B). Cloning of COB and analysis of its deduced amino acid sequence. Summary of the chromosome walk (A and B). (A) Initial mapping placed COB near the LFY locus. Three point crosses using yi, tz and cob-1 plants identified crossover events between the CAPS markers ASBR2 and LFY (vertical lines). Analysis of internal CAPS markers, placed COB in the 74-kb interval between the RLK1 and the 10A10 CAPS markers. (Numbers represent the number of recombinants isolated between the markers shown). The 22 putative genes or open reading frames in this region were sequenced from the cob-1 background until a mutation was revealed in a putative gene (shown in the boxed region; arrows indicate the direction of transcription). (B) Genomic organization of COB (hatched boxes represent exons). Positions of the translational start (ATG) and stop (TAA) of the predicted coding sequence are shown. The position and nucleotide changes in the mutant alleles are also shown.

FIG. 3(C-E). The predicted amino acid sequence is shown directly below the cDNA sequence (C). Numbers to the right refer to the positions of nucleotides or amino acid residues. Triangles represent the positions of introns. Mis-sense point mutations in cob-1, cob-2 and cob-3 alleles are shown above the nucleotide sequence. Underlined is the putative cleavable N-terminal signal sequence as determined with a pSORT algorithm. Underlined and in bold is the motif which, in addition to the N-terminal signal sequence and hydrophilic central portion, appears to meet all of the sequence requirements for processing and GPI linkage according to the GPI prediction algorithm. In bold are the amino acids which would be changed in the mutant alleles. (D) The GPI linkage motif in COB includes: the predicted cleavage site, which is the residue to the left of the cleavage (arrow). +1 and +2 sites immediately following the cleavage site which are part of a 6 amino acid spacer region (boxed), and a 19 amino acid hydrophobic tail (see text for consensus residues). (E) Hydropathy analysis of COB shows the hydrophobic N- and C-termini and the hydrophilic central portion.

FIG. 4(A-F). COB expression analysis. RNA blot analysis (A-C). Total RNA from different organs or plants was isolated and RNA blot analysis was performed with a digoxigenin-labeled COB probe. Equal loading was assessed using ethidium bromide stained 18S and 25S rRNA (data not shown) (A) flowers (lane 1), siliques (lane 2), stems (lane 3), leaves (lane 4), roots (lane 5). (B) wild-type Columbia (lane 1), cob-1 (lane 2), cob-2 (lane 3), cob-3 (lane 4). (C) wild-type WS (lane 1), 35S::COB transgenic in cob-3 (lane 2). The exposure time for the blot in C was significantly shorter than in A and B in order to highlight the different expression levels. In situ hybridization analysis of COB gene expression in wild-type Columbia roots (D-F). Root longitudinal sections were probed with either antisense (D and E) or sense (F) digoxigenin-labeled, in vitro-transcribed RNA from a portion of COB. Upregulation of COB occurs in cells that are undergoing rapid longitudinal expansion (arrowheads in E). Bar=50 µm FIG. 5(A-I). COB protein localization in roots. Immunoblot analysis (A and B). Even numbered lanes are total microsomal membrane fractions, odd numbered lanes are soluble protein fractions. Plants analyzed: 35S::COB transgenic (lanes 1 and 2), wild-type Columbia (lanes 3 and 4), and cob-1 (lanes 5 and 6). (A) Affinity purified COB antibodies (B) antibodies to the tonoplast specific γ-TIP. Arrowheads indicate size in kD. COB immunolocalization in root tissue sections by epifluoresence microscopy (C-I). Roots were incubated with affinity purified anti-COB antibodies and fluorescently labeled secondary antibodies (red signal). In wild type, binding was detected predominately on portions of the longitudinal sides of cells in all cell layers (C), corresponding light image is in (D), (brackets 1 and 2 denote two separate roots). The signal was not continuous around the circumference of the cells, but rather it was found in patches, shown in transverse section (E), corresponding light microscope image is in (F). Analysis of plants overexpressing COB (35S::COB genomic) detected the protein in a more uniform pattern in transverse sections (G), and localized it to the apical and basal sides of cells (white arrowheads) (H) as well as to the longitudinal sides, corresponding light image in (I). (G-I are rescued cob-3 mutants) scale bars E,F,G=25 µm; C,D,H,I=50 µm.

DETAILED DESCRIPTION OF THE INVENTION

COBRA is a protein found in several plant tissues including roots and is involved in controlling the orientation of root expansion during root growth and development. COBRA mutants (cob), particularly, mutants comprising the cob 1–3 alleles, exhibit a CORE phenotype (also referred to as a cob phenotype or cob-like phenotype). The cob phenotype comprises excess radial root body expansion as compared to longitudinal root body expansion (i.e., cob roots exhibit a thicker and fatter morphology than do wild-type roots). Since thicker and fatter roots tend to have an enhanced ability to burrow through dense or packed soil, cob mutant plants may be useful in applications where cultivation of plants in areas comprising this type of soil would be beneficial.

Molecular Biology

In accordance with the present invention there may be employed conventional molecular biology, microbiology, and recombinant DNA techniques within the skill of the art. Such techniques are explained fully in the literature. The following publications are incorporated by reference: e.g., Sambrook, Fritsch & Maniatis, Molecular Cloning: *A Laboratory Manual*, Second Edition Cold Spring Harbor Laboratory Press, Cold Spring Harbor, N.Y., 1989; *DNA Cloning: A Practical Approach*, Volumes I and II (D. N. Glover ed.), 1985; *Oligonucleotide Synthesis* (M. J. Gait ed.), 1984; *Nucleic Acid Hybridization* (B. D. Hames & S. J. Higgins eds.), 1985; *Transcription And Translation* (B. D. Hames & S. J. Higgins, eds.),1984; *Animal Cell Culture* (R. I. Freshney, ed.), 1986; *Immobilized Cells And Enzymes* (IRL Press), 1986; B. Perbal, *A Practical Guide To Molecular Cloning*, F. M. Ausubel et al. (eds.), 1984; *Current Protocols in Molecular Biology*, John Wiley & Sons, 1994.

A "DNA molecule", "nucleic acid molecule", "polynucleotide" or "nucleic acid" refers to the phosphodiester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, may refer to the primary and secondary structure of the molecule, and does not limit it to any particular tertiary forms or to any particular length. A more specific term, "oligonucleotide", refers to a nucleic acid molecule of 20 bases in length, or less. Thus, these terms include double-stranded DNA found, inter alia, in linear (e.g., restriction fragments) or circular DNA molecules (e.g., plasmids) and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A "DNA sequence" or "nucleotide sequence" is a series of nucleotide bases (also called "nucleotides") in DNA and RNA, and means any chain of two or more nucleotides. A nucleotide sequence typically carries genetic information, including the information used by cellular machinery to make proteins. These terms include double or single stranded genomic DNA or cDNA, RNA, any synthetic and genetically manipulated nucleic acid, and both sense and anti-sense nucleic acids. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The term "protein" or "polypeptide" refers to any peptide containing two or more amino acids, modified amino acids, or amino acid derivatives. "Protein" or "polypeptide", by way of example, and without excluding other types of proteins, includes enzymes and structural proteins, preferably the COBRA protein.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is such an element operatively associated with a different gene than the one with which it is operatively associated in nature.

The "nucleic acids" and "nucleic acid molecules" herein may be flanked by natural regulatory sequences (e.g., expression control sequences), or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Nucleic acids may contain one or more additional covalently linked moieties, such as, for example, proteins (e.g., nucleases, toxins, antibodies, signal, peptides, poly-L-lysine, etc.), intercalators (e.g., acridine, psoralen, etc.), chelators (e.g., metals, radioactive metals, iron, oxidative metals, etc.), and alkylators. The nucleic acids may be derivatized by formation of a methyl or ethyl phosphotriester or an alkyl phosphoramidate linkage. Furthermore, the nucleic acids herein may also be modified with a label capable of providing a detectable signal, either directly or indirectly. Exemplary labels include radioisotopes (e.g., $^{32}P$, $^{35}S$, $^{14}C$ or $^{3}H$), fluorescent molecules, biotin, and the like.

The term "host cell" means any cell of any organism that is selected, modified, transformed, grown, or used or manipulated in any way, for the production of a substance by the cell, for example the expression by the cell of a gene or DNA sequence. In specific embodiments of the invention, a host cell is a plant cell or a bacterial cell (e.g., *E. Coli*) which overexpresses or underexpresses COBRA or which comprises a mutated version of COBRA, particularly a cob-1 or cob-3 mutant allele of COBRA.

Proteins are made in the host cell using instructions in DNA and RNA, according to the genetic code. Generally, a DNA sequence having instructions for a particular protein or enzyme is "transcribed" into a corresponding sequence of RNA. The RNA sequence in turn is "translated" into the sequence of amino acids which form the protein. Each amino acid is represented in DNA or RNA by one or more triplets of nucleotides called a codon. The genetic code has some redundancy, also called degeneracy, meaning that most amino acids have more than one corresponding codon corresponding to an amino acid. The amino acid lysine (Lys), for example, can be coded by the nucleotide triplet or codon AAA or by the codon AAG. Codons may also form translation stop signals, of which there are three. Because the nucleotides in DNA and RNA sequences are read in groups of three for protein production, it is important to begin reading the sequence at the correct nucleotide, so that the correct triplets are read. The way that a nucleotide sequence is grouped into codons is called the "reading frame."

The term "gene" refers to a DNA sequence that encodes or corresponds to a particular sequence of amino acids that comprise all or part of one or more proteins, and may or may not include regulatory DNA sequences, such as, for example, promoter sequences, which determine, for example, the conditions under which the gene is expressed. The term "gene" also includes DNA sequences which are transcribed from DNA to RNA, but are not translated into an amino acid sequence. The term COBRA or COB refers to a wild-type COBRA gene; cob refers to a mutated version of COB. Specific examples of cob alleles which are within the scope of the invention are cob-1, cob-2 and cob-3.

A "coding sequence" or a sequence "encoding" an expression product, such as a RNA, polypeptide, or protein, is a nucleotide sequence that, when expressed, results in the production of that RNA, polypeptide, or protein, i.e., the nucleotide sequence encodes an amino acid sequence for that polypeptide or protein. A coding sequence for a protein may include a start codon (usually ATG) and a stop codon. A nucleic acid may also "encode" a gene or DNA sequence in that the nucleotide sequence of the gene or DNA sequence is contained within the nucleic acid.

A "promoter sequence" is a DNA regulatory region capable of binding RNA polymerase in a cell and initiating transcription of a downstream (3' direction) coding sequence. A promoter sequence is bounded typically at its 3' terminus by the transcription initiation site and extends upstream (5' direction) to include bases or elements necessary to initiate transcription at higher or lower levels than that of a promoter without said bases or elements. Within the promoter sequence may be found a transcription initiation site (conveniently defined, for example, by mapping with nuclease S1), as well as protein binding domains (consensus sequences) responsible for the binding of RNA polymerase. Exemplary promoters which may be used with the present invention include the Cauliflower Mosaic Virus 35S promoter, the T7 RNA polymerase promoter, the T3 RNA polymerase promoter or the SP6 RNA polymerase promoter.

A coding sequence may be "under the control of" or "operatively associated with" or "functionally associated with" transcriptional and translational control sequences in a cell when RNA polymerase transcribes the coding sequence into mRNA, which may then be spliced (if it contains introns) and may also be translated into the protein encoded by the coding sequence. In specific embodiments of the invention, a COB promoter is operatively associated with either COB, cob-1, cob-2 or cob-3 or with another non-COB gene. In other specific embodiments, COB, cob-1, cob-2 or cob-3 is operatively associated with a Cauliflower Mosaic Virus 35S promoter. The term "35S" or "35S promoter" refers to the Cauliflower Mosaic Virus 35S promoter.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "gene transfer" refers broadly to any process by which nucleic acids are introduced into a cell.

The term "transfection" or "transformation" means the introduction of a nucleic acid into a host cell. Transfection or transformation may cause the host cell to express a gene or sequence which has been introduced to produce a desired substance, typically a protein coded by the introduced gene or sequence. The introduced gene or sequence may also be called a "cloned" or "foreign" gene or sequence and may include regulatory or control sequences, such as start, stop, promoter, signal, secretion, or other sequences used by a cell's genetic machinery. The gene or sequence may include nonfunctional sequences or sequences with no known function. The DNA or RNA introduced to a host cell can come from any source, including cells of the same genus or species as the host cell, or cells of a different genus or species. For example, introduction of COB, particularly COB functionally associated with a Cauliflower Mosaic Virus 35S promoter, into plant cells, particularly *A. thaliana* cells, would constitute a gene transfer, transfection or transformation process. Introduction of a non-COB gene, which is operatively associated with a COB promoter, into the cells of a plant root or a growing tip of a plant root would be a gene transfer, transformation or transfection process.

The term "vector" means the vehicle by which a DNA or RNA sequence (e.g., a foreign gene) can be introduced into a host cell, so as to transform or transfect the host. Transformation or transfection may promote expression (e.g., transcription and translation) of the introduced sequence. Vectors may include plasmids (e.g., pMAL-c2).

Vectors typically comprise the DNA of a transmissible agent, into which foreign DNA is inserted. A common way to insert one segment of DNA into another segment of DNA involves the use of enzymes called restriction enzymes, which cleave DNA at specific sites (specific groups of nucleotides) called restriction sites, and DNA ligase which joins pieces of DNA, such as a restriction enzyme digested nucleic acid and a restriction enzyme digested plasmid vector, together. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can be readily introduced into a suitable host cell. A plasmid vector often contains coding DNA and promoter DNA and has one or more restriction sites suitable for inserting foreign DNA as well as an origin of replication. Promoter DNA and coding DNA may be from the same gene or from different genes, and may be from the same or different organisms. A large number of vectors, including plasmid and fungal vectors, have been described for replication and/or expression in a variety of eukaryotic and prokaryotic hosts. Non-limiting examples include pKK plasmids (Clonetech; Palo Alto, Calif.), pUC plasmids, pET plasmids (Novagen, Inc., Madison, Wis.), pRSET or pREP plasmids (Invitrogen, San Diego, Calif.), or pMAL plasmids, such as pMAL-c2, (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes.

The term "sequence identity" or "identity" refers to exact matches between the nucleotides or amino acids of two nucleic acids or proteins, respectively, when these sequences are compared. For example, the degree of sequence identity between two nucleic acids may be determined by comparison of the nucleotide sequences of the molecules by use of the BLASTN or CLUSTALW sequence comparison algorithm. Similarly, the amino acid sequences of two proteins may be determined by use of the BLASTP or CLUSTALW sequence comparison algorithm. The BLAST algorithms are publicly accessible, at no cost, at the National Center for Biotechnology Information website (www.ncbi.nlm.nih.gov). The CLUSTALW algorithm is publicly accessible, at no cost, at the European Bioinformatics Institute website (www2.ebi.ac.uk/clustalw/).

As used herein, the terms "sequence similarity", "similarity", "sequence homology" or "homology" refer to both the number of exact matches and conserved matches between the amino acid sequences of two proteins. Amino acid sequence homology between two proteins may be determined with a BLASTP algorithm. A conserved match is a match between two amino acids which are of similar biochemical classification and/or biochemical properties. For example, in the context of a protein sequence comparison, a match of one amino acid with a hydrophobic side group with a different amino acid with a hydophobic side group would be considered a conserved match. Non-limiting examples of biochemical classes which are generally known by those skilled in the art are as follows: hydrophobic (valine, leucine, isoleucine, methionine, phenylalanine, tryptophan, alanine, proline); hydrophilic (histidine, lysine, arginine, glutamic acid, aspartic acid, cysteine, asparagine, glutamine, threonine, tyrosine, serine, glycine); no charge/hydrophilic (cysteine, asparagine, glutamine, threonine, tyrosine, serine, glycine); aromatic (tryptophan, tyrosine, phenylalanine); negatively charged/hydrophilic (aspartic acid, glutamic acid); positively charged/hydrophilic (histidine, lysine, arginine).

The BLAST algorithms are commonly known in the art. The following references regarding the algorithm are herein incorporated by reference in their entireties: BLAST ALGORITHMS: Altschul, S. F., et al., J. Mol. Biol. 215:403–410, 1990; Gish, W., et al., Nature Genet. 3:266–272, 1993; Madden, T. L., et al., Meth. Enzymol. 266:131–141, 1996; Altschul, S. F., et al., Nucleic Acids Res. 25:3389–3402, 1997; Zhang, J., et al., Genome Res. 7:649–656, 1997; Wootton, J. C., et al., Comput. Chem. 17:149–163, 1993; Hancock, J. M., et al., Comput. Appl. Biosci. 10:67–70, 1994; ALIGNMENT SCORING SYSTEMS: Dayhoff, M. O., et al., "A model of evolutionary change in proteins." In *Atlas of Protein Sequence and Structure*, vol. 5, suppl. 3." M. O. Dayhoff (ed.), pp. 345–352, Natl. Biomed. Res. Found., Washington, D.C., 1978; Schwartz, R. M., et al., "Matrices for detecting distant relationships." In *Atlas of Protein Sequence and Structure*, vol. 5, suppl. 3. M. O. Dayhoff (ed.), pp. 353–358,Natl. Biomed. Res. Found., Washington, D.C., 1978; Altschul, S. F., J. Mol. Biol. 219:555–565, 1991; States, D. J., et al., Methods 3:66–70, 1991; Henikoff, S., et al., Proc. Natl. Acad. Sci. USA 89:10915–10919, 1992; Altschul, S. F., J. Mol. Evol. 36:290–300, 1993; ALIGNMENT STATISTICS: Karlin, S., et al., Proc. Natl. Acad. Sci. USA 87:2264–2268, 1990; Karlin, S., et al., Proc. Natl. Acad. Sci. USA 90:5873–5877, 1993; Dembo, A., et al., Ann. Prob. 22:2022–2039, 1994; and Altschul, S. F. "Evaluating the statistical significance of multiple distinct local alignments." *In Theoretical and Computational Methods in Genome Research* (S. Suhai, ed.), pp. 1–14, Plenum, N.Y., 1997.

The present invention comprises an isolated COBRA gene and an isolated COBRA polypeptide and homologues thereof from any plant species. Preferred embodiments of the invention comprise *Arabidopsis thaliana* COBRA (Genbank accession number AF319663), however, COBRA from plants such cotton (Genbank Accession No. AI730765), rice (Genbank Accession No. C74834), soybean (Genbank Accession No. AI416924), tomato (Genbank Accession No. AI773156), maize (Genbank Accession No. AI861761 or AF160475), aspen (Genbank Accession No. AI166150), *Brassica napus* (Genbank Accession No. H74542), *Medicago truncatula* (Genbank Accession No. AW559872), *Lotus japonicus* (Genbank Accession No. AW720520), Ice plant (Genbank Accession No. BE130595) and Loblolly Pine (Genbank Accession No. AA556615) are also within the scope of the present invention. The present invention also comprises COBRA homologues from fungal species such as *Schizosaccharomyces pombe*. A truncated *Arabidopsis thaliana* COBRA cDNA clone which was isolated based on its ability to complement a *S. pombe* mutant deficient in phytochelatin synthesis has the accession No. AJ006787 (Leuchter, R., et al., Plant Physiol. 117: 1526, 1998).

Preferred *Arabidopsis thaliana* COBRA, cob-1 and cob-3 nucleotide and amino acid sequences are summarized in Table 1.

TABLE 1

Sequence Listing Legend

| | |
|---|---|
| COBRA gene nucleotide sequence | SEQ ID NO. 1 |
| COBRA polypeptide amino acid sequence | SEQ ID NO. 4 |
| cob-1 gene nucleotide sequence | SEQ ID NO. 2 |
| cob-1 polypeptide amino acid sequence | SEQ ID NO. 5 |
| cob-3 gene nucleotide sequence | SEQ ID NO. 3 |
| cob-3 polypeptide amino acid sequence | SEQ ID NO. 6 |

The present invention also comprises an isolated polynucleotide comprising 20 or more contiguous nucleotides wherein said polynucleotide encodes a polypeptide which has an amino acid sequence of at least 70% homology or 70% identity to a reference amino acid sequence which is a member selected from the group consisting of SEQ ID NOs.4–6 (i.e., COBRA, cob-1 or cob-3), wherein homology or identity is determined using a BLASTP algorithm, where parameters of the algorithm are selected to give the largest match between the sequences tested over the entire length of the selected reference sequence.

The invention also comprises an isolated polynucleotide comprising 20 or more contiguous nucleotides wherein said polynucleotide comprises at least 70% identity to a reference nucleotide sequence which is a member selected from the group consisting of SEQ ID NOs. 1–3 (i.e., COBRA, cob-1 or cob-3), wherein identity is determined using a BLASTN algorithm, where parameters of the algorithm are selected to give the largest match between the sequences tested, over the entire length of the selected reference sequence.

Additionally, the invention comprises an isolated polypeptide comprising 20 or more contiguous amino acids wherein said polypeptide comprises at least 70% homology or 70% identity to a reference amino acid sequence which is a member selected from the group consisting of SEQ ID NOs. 4–6 (i.e., COBRA, cob-1 or cob-3), wherein homology or identity is determined using a BLASTP algorithm, where parameters of the algorithm are selected to give the largest match between the sequences tested, over the entire length of the selected reference sequence.

The homology or identity determined with the BLASTN and BLASTP algorithms as discussed above is preferably 70% or higher, more preferably 80% or higher, and even more preferably 90% or higher. Most preferably, homology or identity is 90%–100% (e.g., 92%, 95% or 97%).

The invention further provides an isolated polynucleotide which hybridizes under stringent conditions to the polynucleotide encoding a polypeptide comprising an amino acid sequence which is selected from the group consisting of SEQ ID NOs.4–6 as well as an isolated polynucleotide which is complementary to the polynucleotide which encodes the polypeptide. Also included are polynucleotides which hybridize under stringent conditions to a polynucleotide selected from the group consisting of SEQ ID NOs. 1–3 as well as polynucleotides which are complementary to the polynucleotide which hybridizes to the selected polynucleotide.

As used herein, the term "stringent conditions" refers to conditions which permit hybridization between a given polynucleotide and a claimed polynucleotide. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 µg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the polynucleotide of interest and adjusting the if, temperature accordingly. Variations on the above ranges and conditions are well known in the art.

In the following list of genes which are homologues to *A. thaliana* COBRA, the respective numbers in parentheses next to each species indicates the level of nucleotide identity, amino acid identity and amino acid similarity between the homologue and *A. thaliana* COBRA (ND indicates that the comparison with *A. thaliana* COBRA was not done): aspen (44.9, 33.9, 37), cotton (71.2, 81.1, 88.9), ice plant (64, 8, 13.8), tomato (74.8, 85.6, 93.8), rice (67.5, 63.6, 70.8), soybean (75, 82.5, 92.1), *B. napus* (38.8, ND, ND), loblolly pine (46.3, ND, ND), *L. japonicus* (63.2, ND, ND), maize-AI861761 (43.1, ND, ND), *M. truncatula* (69.7, ND, ND).

Methods for Reducing COBRA Activity

COBRA activity may be reduced in a plant cell by any method known in the art. Preferably, COBRA activity is reduced by mutating the COBRA gene in a target cell (e.g., an *A. thaliana* cell) or by reducing expression of COBRA in the cell. COBRA expression may be reduced by methods including RNA interference, antisense RNA expression and cosuppression. The present invention also includes methods for reducing COBRA activity by contacting the protein with an inhibitory substance. Substances which inhibit COBRA may be identified by any assay including those discussed below in "Screening for COB Inhibitors".

Genetic mutation. CORBA activity may be reduced by introducing a genetic change to COBRA including a point mutation or deletion of all or part of the gene. Methods by which a mutation may be introduced to a gene are well known to those skilled in the art. Methods for reducing COBRA activity by genetic mutation include any embodiment wherein the mutation results in a loss of all or part of COBRA activity in a target cell. Preferred embodiments of the invention include methods for reducing COBRA activity by introducing a mutation which results in a cob-1, cob-2 or cob-3 allele.

RNA interference. Expression of COBRA may be reduced by RNA interference. RNA interference has been demonstrated previously to be an effective method by which to reduce expression of a gene in *A. thaliana* by Chang et al., PNAS 83(5):1408–12, 1986 which is herein incorporated by reference. COBRA expression may be reduced by introducing, into a target cell (e.g, a wild-type *A. thaliana* cell), nucleic acid comprising an inverted repeat of the COBRA gene which is operatively associated with a promoter (e.g., a 35S promoter). The inverted repeat comprises COBRA, which is in a sense orientation, optionally followed by a spacer (e.g, an intronic sequence) which is followed by COBRA in an antisense orientation. The sense oriented sequences in the RNA, which are transcribed from the inverted repeat, may fold onto and anneal to the antisense sequences to form a hairpin-like double stranded RNA molecule. The double stranded RNA reduces expression of COBRA protein through a mechanism whose details are not clear.

Antisense. Expression of COBRA (e.g, endogenous COBRA) in a target cell (e.g, a wild-type plant cell) may be reduced by coexpression of antisense COBRA RNA. Methods for regulating expression of a gene by expressing antisense RNA are well known to those skilled in the art. When COBRA mRNA (e.g, expressed endogenously from the COBRA gene) is contacted with antisense COBRA RNA, the strands anneal resulting in double stranded RNA. The presence of the double stranded RNA in the cell leads to a reduction of COBRA protein expression by a mechanism whose details are not clear.

Production of antisense COBRA RNA may be achieved by introducing COBRA DNA into a target cell (e.g, a wild-type *A. thaliana* cell) wherein the antisense strand of the gene is operatively associated with a promoter (e.g, a 35S promoter). The promoter drives transcription of the antisense strand of COBRA DNA into antisense COBRA RNA.

Antisense COBRA RNA may encode all or part of the COBRA gene. In preferred embodiments, antisense COBRA RNA encodes nucleotides 361–766.

Cosuppression. COBRA expression may also be reduced by cosuppression. Methods for reducing expression of genes by cosuppression are well known to those skilled in the art. Cosuppression comprises coexpressing COBRA and a gene comprising nucleotide sequence homology with COBRA (e.g., COBRA from cotton, rice, soybean, tomato, maize, aspen, *Brassica napus, Medicago truncalula, Lotus japonicus*, Ice Plant, Loblolly Pine) within the same cell. Cosuppression leads to a reduction in expression of both genes by a mechanism whose details are not known. The mechanism is believed to operate post-transcriptionally.

Cosuppression may be achieved by introducing a COBRA homologue, operatively associated with a promoter (e.g, a 35S promoter), into a target cell (e.g, a wild-type *A. thaliana* cell). Expression of the COBRA homologue in the target cell along with the endogenous COBRA gene will result in a reduction in expression of both proteins.

Antibodies

According to the invention, COB polypeptide produced recombinantly or by chemical synthesis, and fragments or other derivatives or analogs thereof, including fusion proteins, may be used as an immunogen to generate antibodies that recognize the COB polypeptide. In preferred embodiments, a polypeptide comprising COB residues 67–193 is used to generate antibodies. Such antibodies include, but are not limited to, polyclonal, monoclonal, chimeric, single chain, Fab fragments, and an Fab expression library. The anti-COB antibodies of the invention may be cross reactive, e.g., they may recognize COB from different species. For example, antibodies which recognize COB from *A. thaliana*, rice, soybean, tomato, maize, aspen, *Brassica napus, Medicago truncatula, Lotus japonicus*, Ice Plant and Loblolly Pine are within the scope of the invention. Polyclonal antibodies have a greater likelihood of cross reactivity. Alternatively, an antibody of the invention may be specific for a single form of COB, preferably COB from *A. thaliana*.

Various procedures known in the art may be used for the production of polyclonal antibodies to COB polypeptide or derivatives or analogs thereof. For the production of antibody, various host animals can be immunized by injection with the COB polypeptide, or a derivative (e.g., fragment or fusion protein) thereof, including but not limited to rabbits, mice, rats, sheep, goats, etc. Preferably, the antibodies are generated with New Zealand White rabbits. In one embodiment, the COB polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the COB polypeptide, or fragment, analog, or derivative thereof, any technique that provides for the production of antibody molecules by continuous cell lines in culture may be used. These include but are not limited to the hybridoma technique originally developed by Kohler, et al. (Nature 256:495–497, 1975), as well as the trioma technique, the human B-cell hybridoma technique (Kozbor, et al., Immunology Today 4:72,1983; Cote, et al., Proc. Natl. Acad. Sci. U.S.A. 80:2026–2030, 1983), and the EBV-hybridoma technique to produce human monoclonal antibodies (Cole, et al., in *Monoclonal Antibodies and Cancer Therapy*, Alan R. Liss, Inc., pp. 77–96, 1985). In an additional embodiment of the invention, monoclonal antibodies can be produced in germ-free animals (International Patent Publication No. WO 89/12690, published 28 Dec. 1989).

According to the invention, techniques described for the production of single chain antibodies (U.S. Pat. Nos. 5,476, 786; 5,132,405 and 4,946,778) can be adapted to produce COB polypeptide-specific single chain antibodies. Indeed, these genes can be delivered for expression in vivo. An additional embodiment of the invention utilizes the techniques described for the construction of Fab expression libraries (Huse, et al., Science 246:1275–1281, 1989) to allow rapid and easy identification of monoclonal Fab fragments with the desired specificity for a COB polypeptide, or its derivatives, or analogs.

Antibody fragments which contain the idiotype of the antibody molecule can be generated by known techniques. For example, such fragments include but are not limited to the F(ab¢)2 fragment which can be produced by pepsin digestion of the antibody molecule; the Fab¢ fragments which can be generated by reducing the disulfide bridges of the F(ab¢)2 fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody (e.g. a goat secondary antibody) is labeled (e.g., with AlexaFluor 568). Many means are known in the art for detecting binding in an immunoassay and are within the scope of the present invention. For example, to select antibodies which recognize a specific epitope of a COB polypeptide, one may assay generated hybridomas for a product which binds to a COB polypeptide fragment containing such epitope. For selection of an antibody specific to a COB polypeptide from a particular species of plant, one can select on the basis of positive binding with COB polypeptide expressed by or isolated from cells of that species of plant. In preferred embodiments, anti-COB antibodies are selected and purified by binding to COBRA protein coupled to NHS-activated sepharose.

The foregoing antibodies can be used in methods known in the art relating to the localization and activity of the COB polypeptide, e.g., for Western blotting, imaging COB polypeptide in situ, measuring levels thereof in appropriate physiological samples (e.g., root sections) using any of the detection techniques mentioned above or known in the art.

Screening for COB Inhibitors

The present invention contemplates methods by which substances which modulate COB activity (agonistic or antagonistic) are identified. Any known method may be used to identify substances with COB modulatory activity (e.g., in vivo screens, in vitro screens and computer aided screens). Test compounds may be screened from large libraries of synthetic or natural compounds. Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g., Pan Laboratories (Bothell, Wash.) or MycoSearch (NC), or are readily producible. Additionally, natural and synthetically produced libraries and compounds are readily modified through conventional chemical, physical, and biochemical means (Blondelle, et al., TIBTech 14:60, 1996).

In vivo Assay. A suitable screen for identifying substances which modulate COB comprises analysis of the morphology of plant roots which have been exposed to a candidate substance. Plant roots which lack COB activity exhibit an altered morphology; excess radial to longitudinal growth (cob-like morphology). In one embodiment of the present invention, candidate substances are screened on their ability to cause a cob-like phenotype in wild-type plant roots. In this embodiment, wild-type (COB) plants are exposed to a candidate substance during the development of their root systems. Exposure may occur for any period of time which is sufficient to allow root growth to an extent that root morphology can be easily analyzed. Concurrently, control experiments may be run for comparison. In positive control experiments (when screening for COB antagonists), roots are exposed to a substance which is known to induce a cob-like root morphology. Alternatively, cob mutant (e.g., cob-1 or cob-3) plants can be allowed to grow in the absence of any added substances. In negative control experiments (when screening for COB antagonists), wild-type plants are allowed to grow in the absence of an added substance. Candidate substances which were added to wild-type (COB) plants which are correlated with a greater ratio of radial root growth to longitudinal root growth than the negative control plants can be selected as potential COB inhibitors.

In Vitro Assay. Candidate substances which modulate COB may be identified with in vitro screens which test the ability of the substances to bind to the protein. This method has been published previously in U.S. Pat. Nos. 5,585,277 and 5,679,582 which are herein incorporated by reference in their entireties. A candidate antagonist for a COB target is identified in this method by combining (incubating) the candidate substance with COB, under conditions chosen to cause COB to exist in an appropriate ratio of its folded and unfolded states or to cause the protein to unfold at an appropriate rate. Appropriate ratios and rates are dependent on assay conditions and are determined empirically for binding of COB to the candidate substance. If the candidate substance binds COB, the protein remains in its folded state (does not unfold). Thus, if COB unfolds reversibly, under a given set of conditions, and the candidate substance binds to COB, the relative amount of folded COB will be higher than is the case if the candidate substance does not bind COB (i.e., the relative amount of folded COB is higher in the presence of substance than in its absence). If COB unfolds irreversibly, under a given set of conditions, the rate of unfolding will be slower if the candidate substance binds to COB than if it does not. After a given time of incubation, the ratio of folded COB to unfolded COB is greater than the corresponding ratio if the candidate substance does not bind COB. A related method has also been published in U.S. Pat. No. 6,020,141 which is herein incorporated by reference in its entirety.

Candidate substances which exhibit evidence of binding to COB in the above-described assays may be selected and further analyzed for COB binding activity and the ability to inhibit COB activity.

Rational Design of Agonists/Antagonists. Knowledge of the primary sequence of a COB inhibitory polypeptide fragment (e.g., an inhibitor identified in any of the above-described assays), and the similarity of that sequence with proteins of known function, can provide an initial clue as to the identity of other inhibitors or antagonists. Identification and screening of antagonists is further facilitated by determining structural features of the target protein, e.g., using X-ray crystallography, neutron diffraction, nuclear magnetic resonance spectrometry, and other techniques for structure determination. These techniques provide for the rational design or identification of agonists and antagonists.

Currently, several strategies have been employed to design substances which bind to and modulate activity of a target protein. The most rational and promising approach is based on 3D structure of proteins. This can be understood from the mechanism of drug-receptor binding, which is similar to inserting a key to a lock. The target acts as a lock with one or a few cavities. A candidate substance can bind to the target only if the 3D shape of the substance matches the shape of one of the cavities and there are favorable chemical interactions in the cavity. Hence, given the 3D structure of a protein target, compounds can be designed to fit to a cavity, which is called docking. The best docked compounds can be used as leads to further design substances which modulate COB by testing and optimizing their modulatory effect. Rapid progress in modeling techniques and computer technology have made it possible to do fast speed automated docking on computers. Currently available softwares are capable of docking over 100,000 compounds to a protein in a week, which shows its potential in saving years to find substances which modulate a target protein. These software applications are commonly known in the art.

Uses of cob Plants

Roots from plants lacking in COB activity or roots from plants with low COB activity are generally shorter and fatter than normal, wild-type roots. Without being limited by one particular theory, the altered morphology of cob roots is believed to occur because the roots undergo a greater amount of radial growth as compared to longitudinal growth during development than that of roots from wild-type plants (a cob or CORE phenotype).

Thicker roots (e.g., from cob plants) are more capable of penetrating dense, clay-like soil than thinner and longer wild-type roots. This ability makes cob plants particularly well suited for use in any application wherein enhanced root penetration into dense soil would be beneficial. It has been demonstrated previously by Sarquis, et al., Plant Physiol 96:1171–1177, 1991 (herein incorporated by reference in its entirety) that thicker and fatter Maize roots are more resistant to mechanic impedance (e.g., by dense soil). Any method including production of a plant comprising roots with a higher ratio of radial growth to longitudinal growth is within the scope of the invention. In preferred embodiments, the plant with the higher ratio of radial growth to longitudinal growth is a cob plant, more preferably a plant comprising a cob-1 or cob-3 allele.

Phytoremediation. Cob plants are well suited for phytoremediation applications in areas comprising soil which is too dense to allow wild-type plants to grow. Phytoremediation comprises the use of plants, trees and other vegetation to remove, sequester or degrade environmental contaminants from soil, groundwater, wastewater or landfill leachate. In a phytoremediation process, plants are grown in an area comprising toxic contaminants. As the root system of the plants develop and penetrate the soil, contaminants within the soil are sequestered and incorporated into the cells of the plants. The plants, along with the contaminants which have been incorporated into the plant's cells, are uprooted after they have grown to a given point and destroyed. Heavily contaminated soils often require several rounds of phytoremediation. If an area to be phytoremediated comprises dense, clay-like soil, roots of normal (COB) plants will not be able to deeply penetrate the soil and sequester contaminants effectively; however, cob plants are well suited for phytoremediation of these areas because they comprise thick, fat roots and comprise an enhanced ability to deeply penetrate dense soil.

Crop growth in dense soil. Crop plants comprising cob mutations are well suited for growth in areas with dense soil. Soil compaction is an increasing problem to crop growth. This problem is particularly pronounced in areas where modem, heavy farm equipment is used for if growing and harvesting crops. As the equipment repeatedly passes over an area which is to be cultivated, the soil becomes progressively more compacted and dense. Compaction decreases crop yield potential by restricting root growth and creating a less desirable root environment. As soil is compacted, the number of large soil pores is reduced and soil density is increased. The resultant soil condition restricts the movement of water and air through the soil and increases the soil strength or resistance of the soil to penetration by roots. Since cob mutant plants comprise thicker roots, crops comprising the mutation are well suited for growth in areas with dense soil. The present application anticipates methods comprising growing cob mutant crop plants (e.g., corn, rice, wheat, cotton, tobacco, tomatoes, soy beans and others) in areas comprising dense or clay-like soil.

Enhancement of cotton fiber quality. The quality of fibers obtained from cotton plants (e.g., from *Gossypium hirsutum*) may also be increased by increasing COBRA activity in the plants (e.g., by overexpressing COBRA). Cotton fibers develop from epidermal cells called trichomes that form on cotton embryos. The quality of cotton fibers depends largely on the length of the trichomes. Fibers obtained from short, fat trichomes are typically regarded as poor or low quality whereas fibers obtained from long, thin trichomes are typically regarded as good or high quality fibers. Because COBRA is expressed in leaf trichomes in *Arabidopsis thaliana*, it is also likely to be expressed in cotton embryo trichomes. Enhancing COBRA activity in these cells would make a higher percentage of cotton trichomes long and thin resulting in improved yields of high quality cotton fibers.

EXAMPLES

The following examples are meant to add to the disclosure of the present specification and are, by no means, meant to limit the scope of the present invention.

Example 1

Cloning and Characterization of COBRA

Figure 1B:
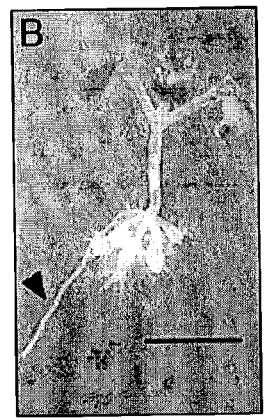
Figure 1C:
Figure 1D:
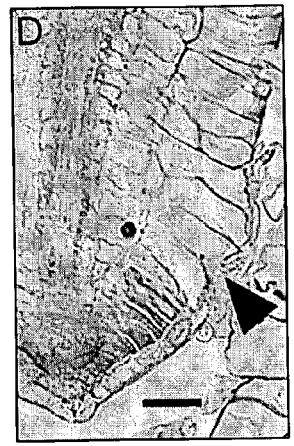

Mutations in COBRA result in mis-oriented cell expansion. Generation of cell files in the *Arabidopsis* root requires initial cells and their immediate progeny to go through a continuous process of division and expansion in the growing region of the root. Cell divisions displace cells upward in the cell file. Wild type cells undergo two distinct expansion phases (FIG. 1A). The first involves both longitudinal and radial expansion, whereby the ultimate root radius is established (FIG. 1C). The second phase is marked by a cessation of radial expansion and a dramatic increase in longitudinal expansion (FIG. 1C; Beemster, G. T., et al., Plant Physiol. 116: 1515–1526, 1998). The region in which cells undergo primarily longitudinal expansion is known as the elongation zone. In striking contrast to wild type, cells in this region of the cob mutant do not undergo highly polarized, longitudinal expansion (FIG. 1B); rather, these cells expand radially to a far greater extent than those of the wild type (FIG. 1D). Although the cob phenotype is most obvious in the epidermal cell layer, where the cell volume is approximately the same as wild type, cells in the cortex and endodermis also expand more radially and less longitudinally than in wild type (Hauser, M. T., et al., Development 121: 1237–1252, 1995). The three alleles of cob we have isolated have a nearly identical phenotype. Although initially characterized as a semi-dominant mutant, the penetrance of the semi-dominant phenotype requires very specific growth conditions; therefore cob generally behaves as a fully recessive mutation. There is no apparent phenotype in the aerial part of the cob mutant when grown in light. There appears to be a slight decrease in hypocotyl length when grown in the dark.

There is a conditional defect in cellulose production in cobra. Because cellulose microfibrils are thought to orient the direction of cell expansion, we investigated whether the role of COBRA in polar longitudinal expansion is mediated through cellulose deposition. Cell walls were isolated from wild type and cob roots. Quantification of crystalline cellulose was determined as cell wall material resistant to acid hydrolysis. Measurements of five independent replicates showed that there was a highly significant difference ($P<0.003$) between wild-type roots which had a mean value of $133\pm28$ μg cellulose/mg cell wall, and cob roots which had a mean value of $89\pm2$ μg cellulose/mg cell wall (Table 2). The decreased amount of cellulose in the root tissue suggests that COB directly or indirectly plays an important role in cellulose deposition.

TABLE 2

Crystalline cellulose analysis. Cellulose was defined as cell wall material resistant to hydrolysis in 2 M trifluoroacetic acid. The cellulose was converted to mono- and oligosaccharides by Saeman hydrolysis, and determined by the phenol-sulfuric acid assay (Dubois, M., et al., Anal. Chem. 28: 350–356, 1956).

| SAMPLE | Average OD (490 nm) | Glucose quantity* (g) | Cell Wall starting material (mg) | Glucose quantity (g)/Cell Wall starting material (mg) |
|---|---|---|---|---|
| Wild type A | 0.757 | 224.58 | 1.8 | 124.77 |
| Wild type B | 0.656 | 194.1 | 1.7 | 114.17 |
| Wild type C | 0.682 | 202.01 | 1.4 | 144.29 |
| Wild type D | 0.276 | 79.79 | 0.5 | 159.58 |
| Wild type E | 0.429 | 125.84 | 1.0 | 125.84 |
| cobra A | 0.494 | 145.33 | 1.7 | 85.49 |
| cobra B | 0.496 | 145.63 | 1.7 | 85.66 |
| cobra C | 0.406 | 118.69 | 1.4 | 84.78 |
| cobra D | 0.170 | 47.58 | 0.5 | 95.16 |
| cobra E | 0.169 | 47.35 | 0.5 | 94.70 |

Figure 1E:
Figure 1F:
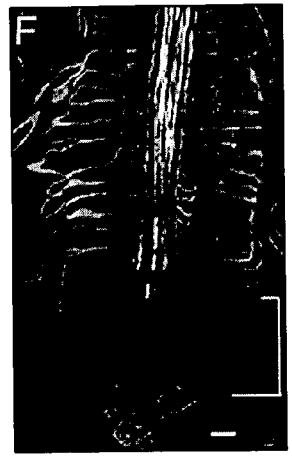

To determine whether there was any spatial specificity to the loss of cellulose in the root, we used polarized light microscopy which detects the presence of crystalline cellulose on a microscopic scale. Under polarized light, the amount of birefringent retardance is a measure of the amount of crystalline cellulose microfibrils in the light path as well as their average degree of alignment (Preston, R. D., *The physical biology of plant cell walls* pp. 75–108. Chapman & Hall, London, 1974). To assess the retardance of cell walls in cob, longitudinal sections of wild-type and mutant roots were observed through a microscope that uses circularly polarized light and digital imaging to produce images in which the intensity at each pixel is linearly proportional to the retardance, regardless of the orientation of the optical axis of the crystallites (Oldenbourg, R., et al., J. Microsc. 180: 140–147, 1995). Thus, cell walls with aligned microfibrils will appear brighter than background for any direction of net alignment. In differentiated regions of the root, retardance in wild type and cob appeared similar; however, in the growing region, the genotypes differed, with retardance in cob being almost undetectable (c.f. FIGS. 1E and F). The decreased retardance indicates a deficit in the amount of crystalline cellulose, or in its net alignment. However, a decrease in alignment is unlikely as the exclusive explanation because retardance decreased not only in walls lying in the plane of the section but also in cross-sectioned walls (compare cross walls in FIGS. 1E and F). A cell wall viewed edge-on (as are the cross walls in FIG. 1) containing random microfibrils gives rise to detectable retardance because all microfibrils are parallel to the wall and therefore possess a net alignment from the point of view of light propagating through the wall from edge to edge.

To confirm that the reduction in retardance was due to a loss in cellulose, we used Fourier Transform Infrared (FTIR) microspectroscopy to detect specific cell wall macromolecules and their orientation by their absorbance of infrared (IR) radiation (McCann, M. C., et al., J. Cell Sci. 106: 1347–1356, 1993). Because the identified alleles of cob are conditional, of interest was the state of cellulose under both restrictive and permissive conditions. Cell walls were prepared from 40 excised roots of wild-type and cob-1 plants, grown in the presence or absence of 3% sucrose. In each case, the pellet of cell walls was spread thinly onto a barium fluoride window, dried, and areas of 50 by 50 μm were selected for analysis by FTIR microspectroscopy (McCann, M., et al., Physiol. Plant. 100, 729–738, 1997). Thirty spectra were obtained from different areas of the barium fluoride window in each case and were compared by exploratory Principal Component Analysis (PCA; Kemsley, E. K., "Chemometric methods for classification problems" in *Discriminant analysis and modelling of spectroscopic data*, pp. 1–47. John Wiley & Sons, Chichester, UK, 1998), a statistical method that reduces the dimensionality of the data from more than a hundred variates (one every 8 $cm^{-1}$ from 1800 to 850 $cm^{-1}$) to only a few PCs. The PCs are ordered in terms of decreasing variance. Each observation (spectrum) has a corresponding set of PC scores, which describes the variance of that spectrum relative to the mean of the population for each PC. The PC scores of the spectra can then be plotted against one another to reveal patterns or structure in the data (Kemsley, E. K., "Chemometric methods for classification problems" in *Discriminant analysis and modelling of spectroscopic data*, pp. 1–47. John Wiley & Sons, Chichester, UK, 1998).

It is possible to mathematically derive a "spectrum" (called a PC loading) from a PC in order to identify molecular factors responsible for the separation of groups of spectra (Chen, L., et al., Plant J. 16, 385–392, 1998; Kemsley, E. K., "Chemometric methods for classification problems" in *Discriminant analysis and modelling of spectroscopic data*, pp. 1–47. John Wiley & Sons, Chichester, UK, 1998). The analysis showed that spectra from wild-type plants grown on sucrose can be separated from spectra of cob-1 grown on sucrose by PC1, accounting for 78% of the total variance in the combined populations (FIG. 2A). The loading for PC1, shown in FIG. 2A, showed characteristics of crystalline cellulose in the fingerprint region (peaks at 991, 1034, 1057; 1111 and 1161 $cm^{-1}$ (Tsuboi, M., J., *Polym. Sci.* 25, 159–171, 1957; Liang, C. Y., et al., J. Polym. Sci. 39, 269–278, 1959), and of protein (peaks at 1650 and 1550 $cm^{-1}$). The former peaks are negatively correlated with the latter. Because the PC scores of spectra of cob-1 cell walls were negative relative to the mean, the data suggest that the cell walls of cob-1 are relatively richer in protein and poorer in cellulose than wild-type cell walls, when the plants have been grown in the presence of sucrose. However, the increase in protein may derive from some cytoplasmic contamination of the cell walls.

Figure 2B:
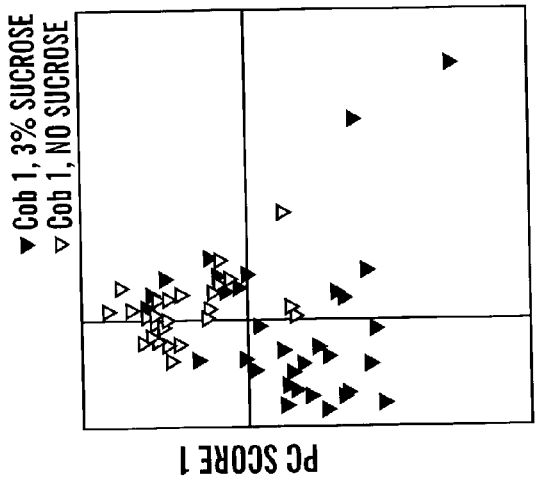
Figure 2B:
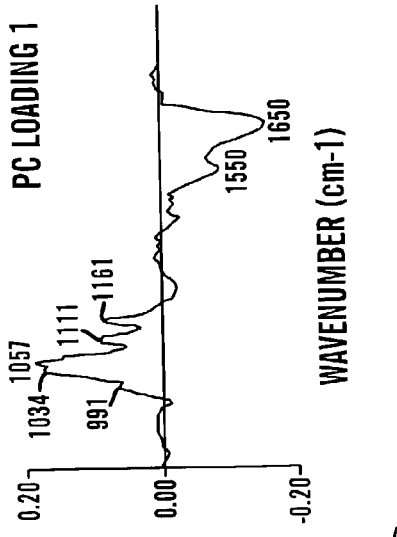
Figure 2A:
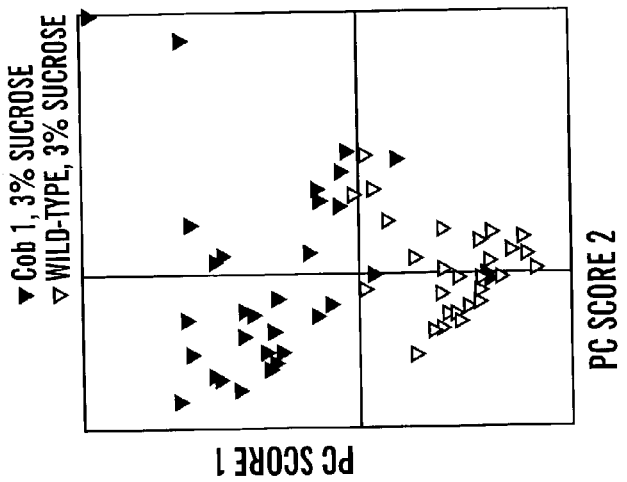
Figure 2A:
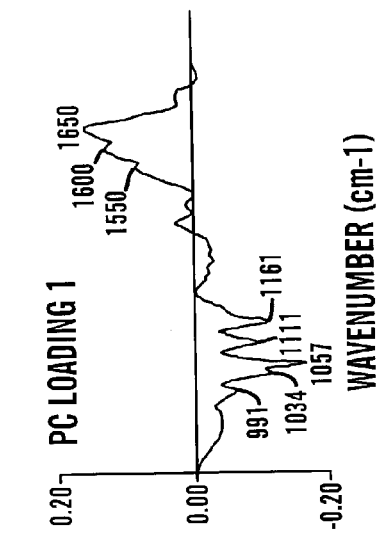

Similarly, a comparison between PC loadings obtained from cob-1 cell walls grown in the presence or absence of sucrose revealed that plants grown in the presence of sucrose were deficient in crystalline cellulose but with increased protein relative to plants grown in the absence of sucrose (FIG. 2B). A slight but consistent difference in cellulose content was observed between wild type and cob-1 grown in the absence of sucrose (data not shown) but of much less magnitude than when the plants were grown in the presence of sucrose. In summary, these data show that the conditional phenotype of cob-1 grown in the presence of sucrose is cellulose-deficient relative to wild-type plants or to cob-1 plants grown in the absence of sucrose. These data suggest the possibility of functional redundancy under slower growth conditions which could compensate at least partially for the loss of COB function.

Figure 3A:
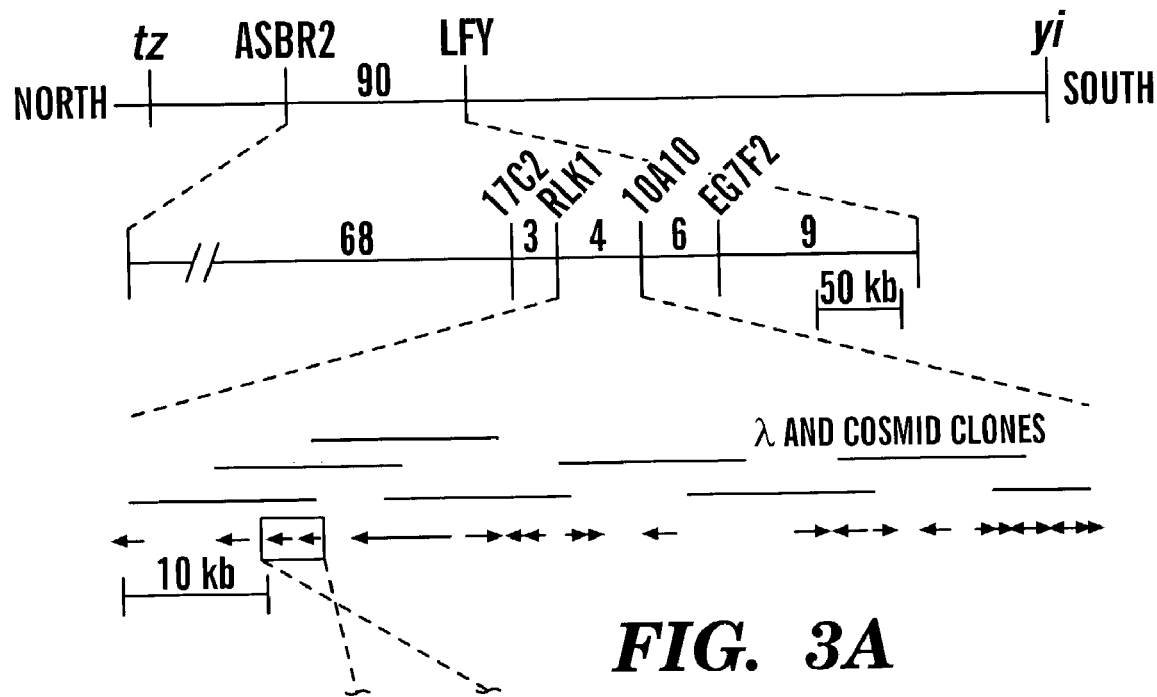
Figure 3B:
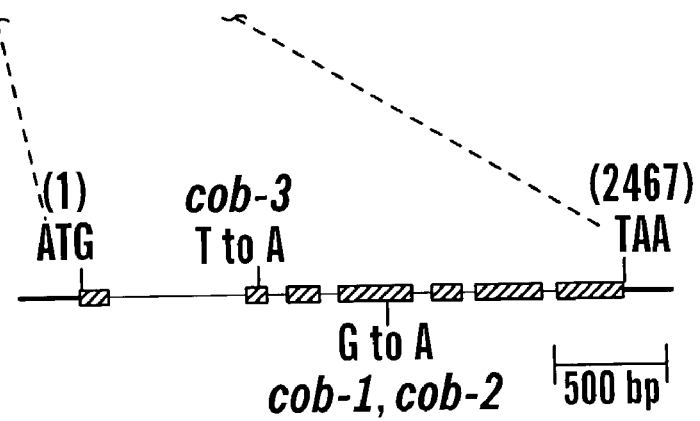

Map-based cloning of COBRA. To better understand COB's role in cell expansion we employed a map-based cloning approach to isolate the COB gene. Three point crosses were used to map the cobra locus to a region on chromosome 5 near the LEAFY locus. Molecular analysis of recombinant plant lines allowed us to map the COBRA locus between the molecular markers RLK1 and 10A10 (FIG. 3A). This region had been physically mapped and covered by a contig of two cosmids and 6 lambda clones (Bender, J., et al., Proc. Natl. Acad. Sci. USA 95: 5655–5660, 1998). Subsequently, the sequence of chromosome 5 was determined through the *Arabidopsis* Genome Initiative allowing cobra to be localized within a 74 kb region. To identify the COBRA gene we sequenced from the cob-1 mutant each of the open reading frames identified in this region. A missense mutation was found in one open reading frame and we then found mutations in the other two cob alleles within the predicted gene (FIG. 3B). Both cob-1 and cob-2 have an identical mutation, suggesting that this may be a mutational hot-spot. However, we cannot rule out the possibility that these are siblings of the same mutant stock. We note that because the molecular lesions in all cob alleles are missense mutations, these alleles may not represent the null phenotype, even though their phenotypes are almost identical.

Rescue of the cob mutant phenotype (both in cob-1 and cob-3) was achieved by transformation of either the genomic region or the COB cDNA driven by the Cauliflower Mosaic Virus 35S promoter, which is constitutively active in most plant tissues (Odell, J. T., et al., Nature 313: 810–812, 1985). Genomic DNA blot analysis and database searching of the complete genome sequence, indicated that there are no genes highly related to COB in *Arabidopsis* (data not shown). However, database comparisons have identified several genes with similar sequences in other plant species but not in other kingdoms (see Materials and Methods, infra). This may indicate that COB is a member of a small plant-specific gene family that has been conserved in plant evolution.

COB encodes a putative GPI-anchored protein. Alignment of the full-length cDNA sequence with genomic sequence indicates that COB is composed of 6 introns and 7 exons (FIG. 3C). The deduced COB gene product is 454 amino acids in length and contains several motifs indicative of subcellular localization (FIG. 3C). These include an N-terminal signal sequence for secretion, a highly hydrophobic C-terminus, a hydrophilic region in between both termini and a stretch of residues found in proteins in which the C-terminus is processed and replaced with a glycosylphosphatidylinositol (GPI) anchor (Udenfriend, S., et al., Annu. Rev. Biochem. 64: 563–591, 1995)

Figure 3D:

The attachment of a GPI moiety to a protein is predicted by conserved amino acid residues at the C-terminus. The site of attachment has been termed "ω" and only Ser, Asn, Ala, Gly, Asp and Cys are found at this site while only Ala, Gly, Thr, or Ser are found at the ω+2 site (Udenfriend, S., et al., Methods Enzymol. 250: 571–581, 1995). The ω+2 residue of known GPI-anchored proteins is usually followed by a spacer of five to seven amino acids rich in charged and/or Pro residues followed by a stretch of 10–30 hydrophobic residues. COBRA meets all of these requirements (FIG. 3D). Although there is only one highly charged residue following the ω+2 residue, this was also found to be true of a bona fide GPI-linked arabinogalactan-protein recently isolated from *Nicotiana alata* (Youl, J. J., et al., Proc. Natl. Acad. Sci. USA 95: 7921-7926, 1998).

Figure 3E:
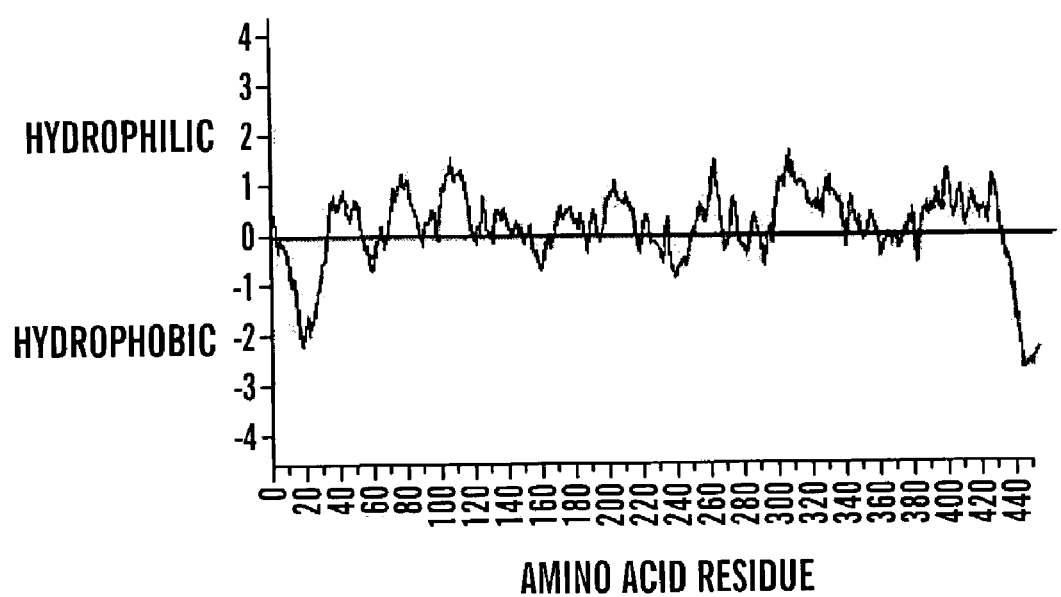

Proteins destined to be GPI-anchored contain hydrophobic sequences at both their N- and C-termini, with the remainder of the protein sequence being essentially hydrophilic (Udenfriend, S., et al., Annu. Rev. Biochem. 64: 563–591, 1995). A hydropathy plot of the deduced amino acid sequence of COBRA confirms these three motifs (FIG. 3E). Apart from their C-terminal domains specifying GPI attachment, the protein moieties attached by GPI-anchors have little in common structurally or functionally (Thompson, G. A., Jr., et al., Prog. Lipid. Res. 39: 19–39, 2000).

Figure 4A:
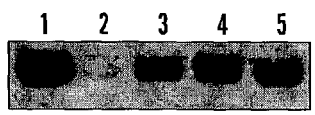
Figure 4B:
Figure 4C:
Figure 4D:
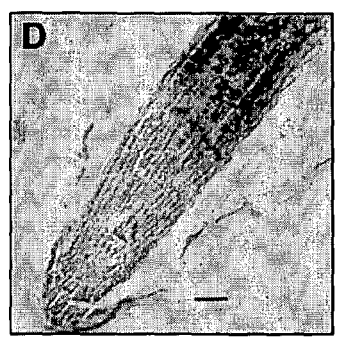
Figure 4E:
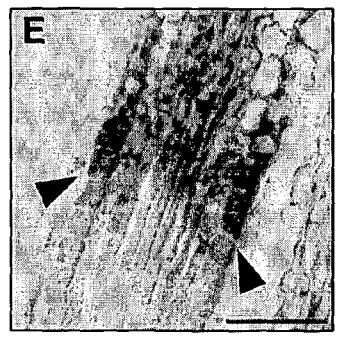
Figure 4F:
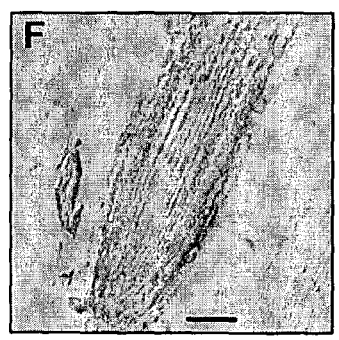

Expression of COBRA RNA and subcellular localization of COBRA protein in the root. To determine if there is organ-specific expression of COB, RNA blot analysis was performed. COB RNA was found in all organs tested, with significantly lower levels in siliques (FIG. 4A). Expression in the mutant alleles appeared similar to wild type (FIG. 4B). As would be expected, plants overexpressing COB contained greatly elevated levels of COB mRNA (FIG. 4C). To analyze the cell-specificity of COB expression, RNA in situ hybridization was performed on longitudinal root sections. Strikingly, expression levels increased dramatically in cells in the elongation zone (FIG. 4D). In fact, expression appeared to increase abruptly as cells entered the zone of rapid longitudinal expansion (FIG. 4E).

Figure 5A:
Figure 5B:
Figure 5C:
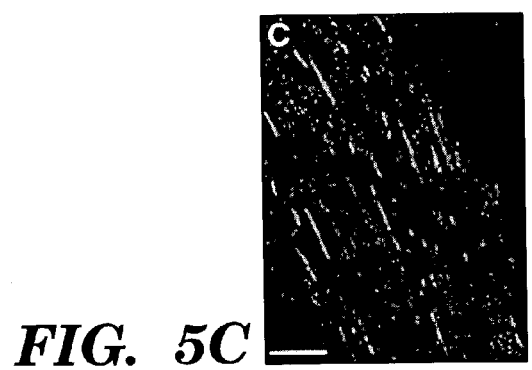
Figure 5D:
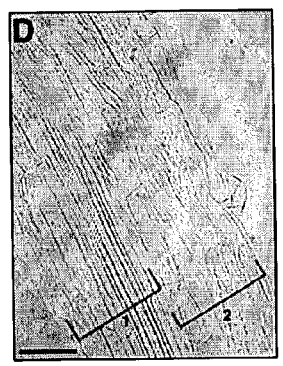
Figure 5E:
Figure 5F:
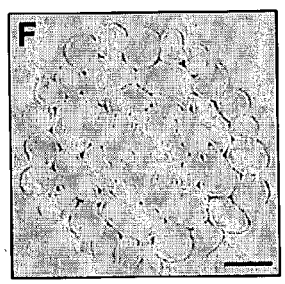

To determine the localization of COB protein both at the cellular and sub-cellular level, we raised polyclonal antisera to a portion of COB fused to the maltose binding protein. The antisera, after affinity purification, were tested against soluble and microsomal protein fractions, the identity of the latter verified by the presence of a tonoplast marker, γ-TIP (FIG. 5B). The anti-COB serum recognized a polypeptide with an apparent molecular mass of 68-kD in the microsomal membranes (FIG. 5A). Although the predicted size of COB based on its amino acid sequence is 49 kD, modifications, such as the potential GPI anchor, may alter its gel mobility. In plants that overexpressed COB, we detected a minor species of polypeptide at approximately 50 kD, not detected in wild type, which may represent the unmodified protein (FIG. 5A). To immunolocalize COB, we incubated the affinity-purified antibodies with longitudinal (FIG. 5C) and transverse (FIG. 5E) sections of wild-type roots. We consistently observed far greater binding of the antibodies to the longitudinal sides of the cells than to the apical or basal sides. Moreover, the signal was detected primarily in discrete regions along the longitudinal cell surfaces, which is consistent with the animal data indicating that GPI linkage can direct proteins to microsomal rafts located on specific sides of polarized cells (Rodriguez-Boulan, E., et al., Annu. Rev. Cell Biol. 8: 395–427, 1992).

Consistent with the RNA expression pattern, protein was undetectable in the distal region of the root tip (data not shown). Antibody binding was first detected somewhat proximal to the region in which RNA is first detected, which probably reflects the time required for detectable amounts of protein to accumulate at the cell surface.

Figure 5G:
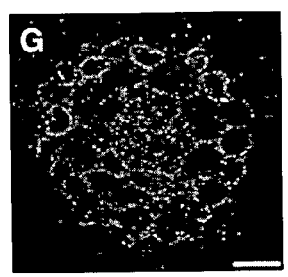
Figure 5H:
Figure 5I:

Ectopic expression of COB. In transgenic plants containing the 35S promoter driving COB cDNA, we detected binding of anti-COB antibodies to the apical and basal cell surfaces as well as to the longitudinal sides of root cells (FIGS. 5G and 5H). Ectopic expression of COB did not appear to alter the expansion profile of these cells. Moreover, the ectopic expression of COB in cells at the root tip which do not normally contain COB did not alter the phenotype in a detectable fashion. The rescue of the cob mutant phenotype in the context of this overexpression suggests that COB is necessary, but not sufficient for highly oriented cell elongation.

Discussion

To achieve correct organ morphology, plants must regulate the orientation and extent of cell expansion. Here we report that cobra, a member of the CORE class of expansion mutants, synthesizes lower amounts of cellulose in the root, with a concomitant altered orientation of cell expansion. The marked reduction in cellulose in the cob root tip, coupled with the lateral expansion of root cells in the mutant, suggest that COB's regulation of oriented cell expansion is associated with the deposition of cellulose.

COB is expressed in cells undergoing highly oriented longitudinal expansion. COB RNA is markedly upregulated in cells in the root elongation zone. In fact, there appears to be a good correlation between increased COB expression and cells entering the zone of rapid longitudinal expansion. This suggests that COB function is not required until the transition to rapid longitudinal expansion. This would argue against a role for COB as a general factor required for cell expansion. Rather, the expression pattern is consistent with a role for COB in regulating oriented cell expansion. COB appears to be expressed in all tissue layers which correlates with abnormal expansion throughout the root (Benfey, P. N., et al., Development 119: 57–70, 1993). Although COB RNA levels are greatly upregulated in the expansion zone, the mutant phenotype extends to the tip of the root. One possible explanation is that the root is capable of altering its overall architecture in response to individual cell shape changes. Support for this hypothesis comes from condition shift experiments. The first cells that expand aberrantly are those entering the zone of rapid longitudinal expansion. At later time points, cells closer to the root tip progressively begin to expand (Hauser, M. T., et al., Development 121: 1237–1252, 1995).

COBRA encodes a putative GPI-anchored protein which is polarly localized. The importance of covalent lipid modification as a means of regulating protein activity or cellular localization is becoming increasingly apparent (Thompson, G. A., Jr., et al., Prog. Lipid. Res. 39: 19–39, 2000). One such lipid modification is the addition of a GPI-anchor to a protein. GPI lipid substitutions have been shown to anchor a diverse group of secreted proteins in the plasma membrane of protozoa, yeast and animals, possibly increasing their lateral mobility (Rodriguez-Boulan, E., et al., Annu. Rev. Cell Biol. 8: 395–427, 1992). While some GPI-anchored proteins have been documented in plants (Schultz, C., et al., Trend. Plant Sci. 3: 426–431, 1998; Sherrier, D. J., et al., Electrophoresis 20: 2027–2035, 1999), none have so far been associated with mutant phenotypes. The COBRA gene product contains a putative GPI-anchor as suggested by its amino acid sequence and its hydropathy plot.

The presence of a GPI-anchor is frequently associated with polar protein sorting in animal cells (Matter, K., et al., Curr. Opin. Cell Biol. 6: 545–554, 1994). There is evidence that GPI-anchors act as sorting signals in the Golgi to target proteins specifically into apical portions of the cell membrane in both neuronal and epithelial cells of mammals (Rodriguez-Boulan, E., et al., Annu. Rev. Cell Biol. 8: 395–427, 1992). Recently, it was also shown in animal cells that not only are GPI proteins specifically targeted within the membrane, but they are organized into micro-domains at the cell surface (Friedrichson, T., et al., Nature 394: 802–805, 1998; Varma, R., et al., Nature 394: 798–801, 1998).

Immunolocalization of COB protein indicates that it is primarily localized in discrete regions along the longitudinal cell surfaces in the root. If it is demonstrated that this is dependent on the GPI-anchor motif this would provide evidence for a shared protein sorting signal between plants and animals.

Evidence from both animal and plants indicates that some GPI-anchored proteins can have the lipid moiety cleaved and thus release the polypeptide which could then act as a diffusible signal. From the protein blot analysis, COB was found primarily in the microsomal fraction which was consistent with the immunolocalization results. Nevertheless, we cannot rule out the possibility that some COB protein is cleaved from its putative GPI-anchor.

Isolation of a partial COB cDNA was reported to complement a S. pombe mutant defective in phytochelatin synthesis (Leuchter, R., et al., Plant Physiol. 117: 1526, 1998). Phytochelatins are small oligopeptides produced enzymatically from glutathione, which are necessary to protect cells from divalent heavy metals, such as cadmium, by binding and rendering them insoluble and non-toxic in the cytoplasm (Ortiz, D. F., et al., EMBO J. 11: 3491–3499, 1992). The partial COB cDNA which was able to confer resistance to cadmium in S. pombe did not contain the first 94 amino acids of COB. These missing amino acids contain the putative N-terminal signal sequence as well as the domain in which the cob-3 mutation is found. Although this reported phytochelatin synthesis activity may not be directly related to COB's in plant function, it is possible that COB binds divalent metals, and this feature could have functional relevance.

COBRA's role in aerial organs. COB RNA is present in stems, leaves, flowers and siliques, yet the cob alleles we have isolated show no apparent light-grown shoot phenotype. One explanation for the lack of a phenotype in the aerial portions of cob mutants is that we do not have a null allele even though the 3 alleles (representing two different mutations) are phenotypically almost identical. Alternatively, there may be genes with functions redundant to COB in the aerial organs. The absence of an aerial phenotype may also be due to cell expansion being controlled by different genetic programs in different organs. The angustifolia and rotundifolia3 mutations result in abnormal expansion only in leaves and floral organs (Kim, G. T., et al., Genes Devel. 12: 2381–2391, 1998). Furthermore, these mutations provide evidence that polar expansion may be regulated by factors that control expansion only in specific directions. The angustifolia mutant has defective cell expansion in the leaf-width direction, resulting in thicker cells, while the rotundifolia3 mutant affects cell elongation in the leaf-length direction.

The ROTUNDIFOLIA gene was shown to encode a member of the P450 cytochrome gene family (Kim, G. T., et al., Genes Devel. 12: 2381–2391, 1998), although the precise mechanism for its function remains to be determined. Another possibility is that the rate of cell expansion in the shoot is generally less than that of the root and that COB function is only required in cells elongating at very high rates.

The conditional nature of the cobra mutation. Under permissive conditions (slower growth), the roots of cob appear to be similar to wild type. We have determined that under these conditions there are nearly wild-type levels of cellulose as well as COB RNA (data not shown). Moreover the conditional phenotype is lost in double mutant combinations with other CORE loci (quill, lion's tail, pompom-1 and pompom-2) (Hauser, M. T., et al., Development 121: 1237–1252, 1995). The recent identification of LION'S TAIL as encoding a member of the endo-1,4-β-D-glucanase (EGase) family, allelic to KORRIGAN(Nicol, F., et al., EMBO J. 17: 5563-5576, 1998) and QUILL as a member of the cellulose synthase gene family allelic to PROCUSTE, (Fagard, M., et al., The Plant Cell, 12, 2000 (in press)) suggests a possible explanation for the conditional phenotype. These proteins may act as part of a complex and/or in the process of cellulose deposition and confer a degree of functional redundancy.

Overexpression of COB. Expression of COB under the control of the constitutive 35S promoter was able to rescue the cob mutant phenotype. However, expression from this construct in wild-type plants did not result in any detectable phenotype. This result suggests the existence of other proteins that are necessary for COB function, and these co-factors are limiting either spatially or quantitatively.

When driven by the 35S promoter, COB levels are elevated and COB protein is now found more uniformly distributed on the cell surface. The generation and maintenance of distinct cell surface polarity involves extensive molecular sorting (Matter, K., et al., Curr. Opin. Cell Biol. 6: 545–554, 1994) and perhaps the mechanisms which localize COB cannot keep up with the over-production in the transgenic lines. The mislocalization without any aberrant phenotype is further evidence that COB is necessary, but not sufficient to cause a shift in expansion.

Possible models for COB's role in oriented cell expansion. The specification of cell shape requires regulation of the production and arrangement of cell wall constituents. The deficit in cellulose in cobra indicates that the COBRA gene product is either directly or indirectly involved in cellulose synthesis. However, the role of COB is likely to be more complicated than simply providing a component of the cellulose deposition machinery. The cob phenotype is distinct from the phenotypes of the mutants rsw1 (Arioli, T., et al., Science 279: 717–720, 1998) and procuste (Fagard, M., et al., The Plant Cell, 12, 2000 (in press)), in which the affected genes encode catalytic subunits of cellulose synthase, or of korrigan, in which the affected gene encodes an endo-glucanase that is involved in cellulose synthesis (Nicol, F., et al., EMBO J. 17: 5563–5576, 1998). The cob phenotype suggests that COB functions specifically in the transition between the arrest of radial expansion and the initiation of the rapid longitudinal expansion phase. We suggest two possible models for COB function. The localization of COB to the longitudinal surfaces of expanding cells in a non-uniform fashion raises the possibility that COB acts to recruit cellulose synthesizing complexes to discrete positions on the cell surface. This could allow for highly polarized longitudinal expansion in the root. Alternatively, COB may act through an, as yet, undefined mechanism to alter the orientation of cell expansion by resisting radial wall expansion and/or promoting longitudinal wall expansion. In this model, the effect on cellulose deposition in the mutant would be indirect resulting from insufficient numbers of cellulose synthesizing complexes being recruited to keep pace with the outward expansion of the cell.

Materials and Methods

Growth of plants. *Arabidopsis* plants were grown as described previously (Benfey, P. N., et al., Development 119: 57–70, 1993). Except as noted, plant growth medium was supplemented with 4.5% sucrose, and the pH (5.7) was adjusted after the addition of agar. Cob-1 and cob-2 are in the Columbia ecotype and cob-3 is in the Wassilewskija (W.S.) ecotype.

Cellulose analysis. Two to five grams of five-day old seedling root tissue were frozen at −80° C., ground in a glass-glass grinder and incubated in 95% ethanol for 30 min at 65° C. Samples were cooled to room temperature and pelleted (5000 rpm). Pellets were washed twice in 95% ethanol and then extracted overnight in methanol/chloroform (⅔:v/v). Extracted material was pelleted and washed five times in 95% ethanol. The cell wall pellet was dried overnight at 65° C., and then freeze dried. Wall material (0.5 to 1.8 mg) was hydrolyzed in 1 ml of 2 M trifluoroacetic acid at 120° C. for 90 min. The undigested material, mostly crystalline cellulose, was pelleted (4000 rpm).

The cellulosic material was digested to glucose monomers by Saeman hydrolysis as described in Em; Shatalov, A. A., et al., Carbohydr. Res. 320: 93–99, 1999, and total sugar was determined by the phenol-sulfuric method (Dubois, M., et al., Anal. Chem. 28: 350–356, 1956).

Polarized Light Microscopy. To assess birefringent retardance of the cell walls, roots were fixed and embedded in plastic as described below and sectioned at 3 μm thickness. Retardance was assessed on a polarized-light microscope (Jenapol, Zeiss) equipped for circularly polarized light quantitative digital imaging (LC pol Scope; Cambridge Research Instruments). For plastic embedding, one to two week old seedlings were fixed in 4% paraformaldehyde in PBS overnight at 4° C. and rinsed 2 times in PBS. The roots were subsequently pre-embedded in 1% agarose, dehydrated in ethanol, and infiltrated with Historesin (Technovit 7100, Kulzer). Plastic sections were mounted on Superfrost slides (Fisher). In FIG. 1D, the root was stained by submersion into 0.05% toluidine blue for 3 minutes.

FTIR spectroscopy. Cell wall material was prepared by excising roots from 40 plants of each of Columbia and cob-1, grown on 3% or no sucrose. The plants were ground in an Eppendorf tube using a miniature homogenizer. The homogenate was centrifuged at 13,000 rpm for 10 min and the supernatant discarded. The pellet was re-suspended in distilled water and washed three times. The final pellet was re-suspended in 100 μl of distilled water and pipetted onto a barium fluoride window.

The wet pellets of cell walls were dried at 37° C. for 1 h on barium fluoride windows (Crystran Ltd., UK). The windows were supported on the stage of a UMA500 microscope accessory of a Bio-Rad FTS175c FTIR spectrometer equipped with a liquid nitrogen-cooled mercury cadmium telluride detector. An area of wall (50×50 μm) was selected for spectral collection in transmission mode. One hundred and twenty-eight interferograms were collected with 8 cm⁻ resolution and co-added to improve the signal-to-noise ratio for each sample. Thirty spectra were collected from different areas of each window. All data sets were baseline-corrected and area-normalized before statistical methods were applied. Exploratory PCA was carried out using Win-Discrim software (Kemsley, E. K., "Chemometric methods for classification problems" in *Discriminant analysis and modelling of spectroscopic data*, pp. 1–47. John Wiley & Sons, Chichester, UK, 1998). Reference IR absorption spectra of cellulose were used for peak assignments (Tsuboi, M., J. Polym. Sci. 25, 159–171, 1957; Liang, C. Y., et al., J. Polym. Sci. 39, 269–278, 1959).

Cloning of COB. Initial analysis of 120 $F_2$ plants from a cob-1 (Col)×wild type (Ler) cross positioned the COB locus on the distal portion of chromosome 5, 0.63 cM north of the LEAFY(LFY) cleaved amplified polymorphic sequence (CAPS) molecular marker (Konieczny, A, et al., Plant J. 4: 403–410, 1993). Initial genetic data indicated that COB was contained in the approximately 15 cM region between the YI (yellow inflorescence) and TZ (thiazole requiring) loci. Three point crosses between the yi tz double mutant (Ler) and cob-1 (Col) were preformed to generate recombination events on both sides of the COB gene. Thirteen $F_1$ plant lines were propagated to the $F_2$ generation and approximately 16,000 plants were scored for the yi phenotype in the absence of exogenous thiamine (needed by tz plants). A total of 383 plants were scored in this category, which is indicative of a recombination event between yi and tz.

Because the mutations in cob-1(cob-2) and cob-3 created polymorphisms with NlaIV and AluI respectively, we were able to confirm the mutations by PCR of genomic DNA and restriction analysis. PCR amplification and digestion was performed two independent times.

Southern blotting was performed as described (Sambrook, F., et al., *Molecular cloning. A laboratory manual*. Cold Spring Harbor Laboratory Press, N.Y., 1989). *Arabidopsis* genomic DNA was isolated according to the procedure described by (Ausubel, et al., *Current protocols in molecular biology*. John Wiley & Sons, Inc., New York, N.Y., 1987). For detection of DNA, nucleic acids were immobilized onto nylon membranes by UV crosslinking and were hybridized with a single-stranded digoxigenin (DIG)-labeled probe made using PCR (Finckh, U., et al., Biotechniques 10: 35–36, 1991).

The hydropathy plot was generated using the Weizmann Institute of Sciences Genome and Bioinformatics web site with Kyte and Doolittle parameters and a window size of seventeen amino acids.

RNA analysis. RNA was isolated using a phenol extraction protocol (Jackson, A. O., et al, Plant Physiol 57:5–10, 1976) or the RNeasy kit (Qiagen; Valencia, Calif.). For RNA blot analysis: prehybridization, hybridization, and detection were performed as described in Di Laurenzio, L., et al., Cell 86: 423–433, 1996. Blots were hybridized with a single-stranded digoxigenin (DIG)-labeled probe (Finckh, U., et al., Biotechniques 10: 35–36, 1991). To make the probe, a single stranded 975 bp anti-sense COB DNA fragment was created by PCR (bp 1688 to 2663, including 64 bases of the 3' untranslated region).

In situ hybridization analysis was performed as described in Di Laurenzio, L., et al., Cell 86: 423–433, 1996. To generate COB specific anti-sense and sense RNA probes, a PCR up amplified DNA fragment of the COB cDNA (base pairs 220 to 766) was inserted into pCR2.1 (Invitrogen). After digestion with BamHI a fragment (base pairs 361 to 766) was subcloned into the BamHI site of pBluescript II SK (+) (Stratagene), in both orientations. After linearizing each construct with NotI, in vitro transcription and DIG-labeling using the DIG RNA Labeling Kit (Boehringer Mannheim) was performed.

35S::COB transgene and *Agrobacterium*-mediated transformation. The 35S::COB cDNA and genomic constructs were made by placing sequences between the 35S promoter and the nopaline synthase polyadenylation sequence. To make the 35S:: COB cDNA construct, the full length cDNA was excised from IPRL2 (EST 163D2T7, Genbank accession R29979) as a HindIII, EcoRI fragment, subcloned into pBluescript II KS (+), excised by XbaI, XhoI and inserted into the corresponding sites of the plasmid V7 (from Dr. T. Brears). The 35S:: COB genomic construct was made using a 4.1 kb HindIII fragment (containing the entire COB genomic sequence+2 kb downstream) of a 1 clone from the chromosome walk, subcloned into the HindIII site of pBluescript II KS (+). The fragment was excised by digestion with HindIII, XbaI and inserted into the corresponding sites of the plasmid W104 (from Dr. T. Brears). Expression plasmids were transformed into cob-1 and cob-3 plants by the floral dipping method (Clough, S. J., et al., Plant J. 16: 735–743, 1998).

Production of COB specific polyclonal antiserum. To generate COB-specific polyclonal antibodies, we ligated, after PCR amplification and addition of a 5' EcoRI site and a 3' HindIII site, a fragment of the COB cDNA encoding amino acids 67 through 193 into the bacterial expression vector pMAL-c2 (New England BioLabs; Beverly, Mass.). After expression in *E. coli* strain BL21, the recombinant protein was affinity purified on an amylose resin column (New England BioLabs; Beverly, Mass.), according to manufacturer's instructions, and injected into two New Zealand White rabbits (Covance; Princeton, N.J.). Polyclonal antisera were affinity purified against the recombinant COB protein coupled to NHS-Activated Sepharose 4 fast flow (Amersham Pharmacia Biotech; Piscataway, N.J.), according to manufacturer's instructions.

Immunolocalization. Microsome fractions were prepared as in Jinn, T. L., et al., Genes Devel. 14:108–117, 2000. Isolation of microsomes was assessed using the microsome-specific anti a-TIP antibody (Johnson, K. D., et al., Plant Cell 2:525–532, 1990). Protein samples were resolved by SDS-PAGE as in (Laemmli, U.K., Nature 227: 680–685, 1970). Ten to 14 day old plants were grown under restrictive conditions (Benfey, P. N., et al., Development 119: 57–70, 1993), fixed, embedded and sectioned at 8 mm. Antibody incubation and immunohistochemistry were performed as described (Di Laurenzio, L., et al., Cell 86: 423–433, 1996), with the following modifications: root sections were incubated with affinity purified anti-COB at room temperature for 1 h. Incubation with secondary antibodies conjugated to Alexa Fluor 568 (Molecular Probes, 1:250) was done at ambient temperature for 45 min to 1 h. Goat serum was added to all incubations (1:50:v/v).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

We claim:

1. An isolated polynucleotide encoding a COBRA protein, wherein said polynucleotide encodes a polypeptide comprising the amino acid sequence of SEQ ID NO:4, or wherein said polynucleotide comprises the nucleotide sequence of SEQ ID NO:1.

2. The isolated polynucleotide of claim 1 which encodes a polypeptide which has the amino acid sequence of SEQ ID NO:4.

3. The isolated polynucleotide of claim 1 comprising the nucleotide sequence of SEQ ID NO:1.

4. The isolated polynucleotide of claim 1 wherein the polynucleotide is a member selected from the group consisting of DNA and RNA.

5. The isolated polynucleotide of claim 1, wherein said polynucleotide is operatively associated with a foreign promoter.

6. The polynucleotide of claim 5 wherein the foreign promoter is the Cauliflower Mosaic Virus 35S promoter.

7. An isolated host cell transformed or transfected with the polynucleotide of claim 1.

8. The isolated host cell of claim 7, wherein said polynucleotide encodes a polypeptide comprising the amino acid sequence of SEQ ID NO:4.

9. The isolated host cell of claim 7, wherein said polynucleotide comprises the nucleotide sequence of SEQ ID NO:1.

10. A transgenic plant comprising the polynucleotide of claim 5.

11. The plant of claim 10 wherein the promoter is the Cauliflower Mosaic Virus 35S promoter.

12. The plant of claim 9 wherein the plant is *Arabidopsis thaliana*.

13. A method for producing a COBRA protein which method comprises introducing the polynucleotide of claim 1 into an isolated host cell and expressing the COBRA protein in said host cell.

* * * * *